(12) United States Patent
Popp et al.

(10) Patent No.: US 8,176,573 B2
(45) Date of Patent: May 15, 2012

(54) BOXER SHORTS AND PROCESS OF MAKING BOXER SHORTS FROM ONE OR MORE WEBS

(75) Inventors: Robert Lee Popp, Hortonville, WI (US); Joseph Daniel Coenen, Kaukauna, WI (US); Heather Schenck Mortell, Neenah, WI (US); James Bassey Pinkney, Appleton, WI (US); Lars Nilsen Nordang, Neenah, WI (US); James Richard Schermerhorn, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1176 days.

(21) Appl. No.: 10/954,990

(22) Filed: Sep. 30, 2004

(65) Prior Publication Data

US 2005/0102735 A1  May 19, 2005

Related U.S. Application Data

(63) Continuation-in-part of application No. 10/314,915, filed on Dec. 9, 2002, now abandoned.

(30) Foreign Application Priority Data

Sep. 8, 2003  (WO) ...................... PCT/US03/28238
Nov. 18, 2003  (AR) ................................... 030104263

(51) Int. Cl.
*A41B 9/00* (2006.01)
(52) U.S. Cl. ............. 2/403; 2/400; 2/401; 2/404; 2/228; 2/238
(58) Field of Classification Search ............... 2/403, 404, 2/401, 400, 228, 238; 604/400
See application file for complete search history.

(56) References Cited

U.S. PATENT DOCUMENTS 478,281 A  7/1892  Hamilton et al.
(Continued)

FOREIGN PATENT DOCUMENTS

AT  168478 B  6/1951
(Continued)

OTHER PUBLICATIONS

Printed materials (3 pages) showing pull-on diapers disclosed at a trade show Apr. 27-29, 2004 in Miami Beach, Florida, U.S.A.

(Continued)

*Primary Examiner* — Alissa Tompkins
(74) *Attorney, Agent, or Firm* — Armstrong Teasdale LLP

(57) ABSTRACT

A boxer-style pant and methods of making a boxer-style pant having side seams and hanging legs. At least a portion of each of the hanging legs may be non-planar in an uncontracted state prior to formation of the side seams. The methods each involve providing at least one web. In some methods, a crotch panel is bonded to first and second regions of the web between two leg openings, and a distance between bonded regions of upper and lower edges of the crotch panel, measured parallel to a longitudinal axis of the pant, is shorter along a central region of the crotch panel and longer in distal regions of the crotch panel, such that the bonded region results in a bow-tie-shaped crotch panel. In some methods, a crotch region of the web is folded and stabilized along a longitudinal centerline of the web. In some methods, leg extensions are attached to at least a portion of each of two leg openings. Front and back regions may be joined together to form the side seams. An absorbent structure may be attached to the web.

20 Claims, 22 Drawing Sheets

U.S. PATENT DOCUMENTS

| | | | |
|---|---|---|---|
| 1,577,409 A * | 3/1926 | Rand | 2/401 |
| 1,664,298 A | 3/1928 | Katz | |
| 1,971,558 A | 8/1934 | Goodman | |
| 2,030,306 A | 2/1936 | Lain | |
| 2,032,982 A | 3/1936 | Gerstman | |
| 2,088,302 A | 7/1937 | McKeever | |
| 2,116,822 A | 5/1938 | Berger | |
| 2,131,808 A | 10/1938 | Joa | |
| 2,242,526 A | 5/1941 | Kneibler | |
| 2,252,019 A | 8/1941 | Meinecke et al. | |
| 2,319,138 A | 5/1943 | Kneibler | |
| 2,391,641 A | 12/1945 | O'Hern | |
| 2,435,945 A | 2/1948 | Redmond | |
| 2,450,789 A | 10/1948 | Frieman | |
| 2,522,510 A | 9/1950 | Fridolph | |
| 2,538,596 A | 1/1951 | Sheridan | |
| 2,675,806 A | 1/1954 | Bram | |
| 2,711,735 A | 6/1955 | Sabo | |
| 2,838,047 A | 6/1958 | Sidnell | |
| 2,842,129 A | 7/1958 | Ernstorff | |
| 2,859,752 A | 11/1958 | Haber | |
| 3,245,407 A | 4/1966 | Mason | |
| 3,338,992 A | 8/1967 | Kinney | |
| 3,341,394 A | 9/1967 | Kinney | |
| 3,418,660 A | 12/1968 | Shumate | |
| 3,502,538 A | 3/1970 | Petersen | |
| 3,502,763 A | 3/1970 | Hartmann | |
| 3,542,615 A | 11/1970 | Dobo et al. | |
| 3,611,443 A | 10/1971 | Braun | |
| 3,648,699 A | 3/1972 | Anderson et al. | |
| 3,678,516 A | 7/1972 | Backer | |
| 3,692,618 A | 9/1972 | Dorschner et al. | |
| 3,714,946 A | 2/1973 | Rudes | |
| 3,739,398 A | 6/1973 | Sarmiento | |
| 3,802,817 A | 4/1974 | Matsuki et al. | |
| 3,806,007 A | 4/1974 | Grantham | |
| 3,844,282 A | 10/1974 | King | |
| 3,859,667 A | 1/1975 | Roy | |
| 3,869,999 A | 3/1975 | Richter | |
| 3,920,237 A | 11/1975 | Grantham | |
| 4,059,257 A | 11/1977 | Grantham | |
| 4,081,301 A | 3/1978 | Buell | |
| 4,100,324 A | 7/1978 | Anderson et al. | |
| 4,106,125 A | 8/1978 | Palumbo | |
| 4,114,621 A | 9/1978 | Mims, Jr. | |
| 4,116,892 A | 9/1978 | Schwarz | |
| 4,145,763 A | 3/1979 | Abrams et al. | |
| 4,223,059 A | 9/1980 | Schwarz | |
| 4,227,952 A | 10/1980 | Sabee | |
| 4,280,230 A | 7/1981 | LaFleur | |
| 4,284,454 A | 8/1981 | Joa | |
| 4,285,100 A | 8/1981 | Schwarz | |
| 4,300,241 A | 11/1981 | Shaull | |
| 4,310,929 A | 1/1982 | Finlay | |
| 4,327,448 A | 5/1982 | Lunt | |
| 4,338,939 A | 7/1982 | Daville | |
| 4,340,563 A | 7/1982 | Appel et al. | |
| 4,368,565 A | 1/1983 | Schwarz | |
| 4,392,259 A | 7/1983 | Bredo | |
| 4,397,704 A | 8/1983 | Frick | |
| 4,417,938 A | 11/1983 | Sigl | |
| 4,449,254 A | 5/1984 | Fogg | |
| 4,543,141 A | 9/1985 | Bradley et al. | |
| 4,555,245 A | 11/1985 | Armbruster | |
| 4,597,110 A | 7/1986 | Smith, Sr. et al. | |
| 4,608,115 A | 8/1986 | Schroth et al. | |
| 4,644,945 A | 2/1987 | Thorner | |
| 4,646,362 A | 3/1987 | Heran et al. | |
| 4,650,530 A | 3/1987 | Mahoney et al. | |
| 4,655,760 A | 4/1987 | Morman et al. | |
| 4,663,106 A | 5/1987 | Pomplun et al. | |
| 4,663,220 A | 5/1987 | Wisneski et al. | |
| 4,665,306 A | 5/1987 | Roland et al. | |
| 4,671,793 A | 6/1987 | Hults et al. | |
| 4,675,918 A | 6/1987 | O'Brien | |
| 4,704,116 A | 11/1987 | Enloe | |
| 4,745,636 A | 5/1988 | Lunt | |
| 4,771,483 A | 9/1988 | Hooreman et al. | |
| 4,786,346 A | 11/1988 | Ales et al. | |
| 4,805,243 A | 2/1989 | Gibbens et al. | |
| 4,816,094 A | 3/1989 | Pomplun et al. | |
| 4,835,795 A | 6/1989 | Lonon | |
| 4,847,134 A | 7/1989 | Fahrenkrug et al. | |
| 4,870,958 A | 10/1989 | Webster | |
| 4,872,221 A | 10/1989 | Stone, III | |
| 4,875,240 A | 10/1989 | Barrett | |
| 4,883,549 A | 11/1989 | Frost et al. | |
| 4,892,536 A | 1/1990 | DesMarais et al. | |
| 4,895,568 A | 1/1990 | Enloe | |
| 4,935,021 A | 6/1990 | Huffman et al. | |
| 4,946,539 A | 8/1990 | Ales et al. | |
| 4,955,880 A | 9/1990 | Rodriquez | |
| 4,964,860 A | 10/1990 | Gipson et al. | |
| D315,050 S | 3/1991 | Bush et al. | |
| 5,014,364 A | 5/1991 | Orr | |
| 5,022,240 A | 6/1991 | Peleg | |
| 5,046,272 A | 9/1991 | Vogt et al. | |
| 5,052,058 A | 10/1991 | Mueller | |
| 5,067,178 A | 11/1991 | Katchka | |
| 5,087,253 A | 2/1992 | Cooper | |
| 5,103,505 A | 4/1992 | Llorens | |
| 5,135,522 A | 8/1992 | Fahrenkrug et al. | |
| 5,147,487 A | 9/1992 | Nomura et al. | |
| 5,171,388 A | 12/1992 | Hoffman et al. | |
| 5,187,817 A | 2/1993 | Zolner | |
| 5,210,882 A | 5/1993 | Moretz et al. | |
| 5,217,782 A | 6/1993 | Moretz et al. | |
| 5,226,992 A | 7/1993 | Morman | |
| D341,243 S | 11/1993 | Costella et al. | |
| 5,297,296 A | 3/1994 | Moretz et al. | |
| 5,303,424 A | 4/1994 | Cromartie | |
| 5,306,536 A | 4/1994 | Moretz et al. | |
| 5,315,716 A | 5/1994 | Baum | |
| 5,315,717 A | 5/1994 | Moretz et al. | |
| 5,370,634 A | 12/1994 | Ando et al. | |
| 5,379,462 A | 1/1995 | Morgan et al. | |
| 5,382,246 A | 1/1995 | Kawano | |
| 5,435,014 A | 7/1995 | Moretz et al. | |
| 5,445,628 A | 8/1995 | Gipson et al. | |
| 5,500,063 A | 3/1996 | Jessup | |
| 5,545,158 A | 8/1996 | Jessup | |
| 5,549,593 A | 8/1996 | Ygge et al. | |
| 5,554,149 A | 9/1996 | O'Donnell | |
| 5,556,504 A | 9/1996 | Rajala et al. | |
| 5,566,392 A | 10/1996 | Dzelzkains | |
| D377,557 S | 1/1997 | Jagger | |
| 5,649,913 A | 7/1997 | Cohen | |
| D382,386 S | 8/1997 | Malone | |
| 5,669,902 A | 9/1997 | Sivilich | |
| 5,669,996 A | 9/1997 | Jessup | |
| 5,690,626 A | 11/1997 | Suzuki et al. | |
| 5,690,627 A | 11/1997 | Clear et al. | |
| 5,704,071 A | 1/1998 | Barclay et al. | |
| 5,716,478 A | 2/1998 | Boothe et al. | |
| 5,718,003 A | 2/1998 | Gwinn | |
| 5,733,401 A | 3/1998 | Linman et al. | |
| 5,746,730 A | 5/1998 | Suzuki et al. | |
| 5,755,902 A | 5/1998 | Reynolds | |
| 5,759,340 A | 6/1998 | Boothe et al. | |
| 5,790,983 A | 8/1998 | Rosch et al. | |
| 5,827,260 A | 10/1998 | Suzuki et al. | |
| 5,853,405 A | 12/1998 | Suprise | |
| 5,876,394 A | 3/1999 | Rosch et al. | |
| 5,891,122 A | 4/1999 | Coates | |
| D408,964 S | 5/1999 | Hernandez | |
| 5,906,604 A | 5/1999 | Rönnberg et al. | |
| 5,906,879 A | 5/1999 | Huntoon et al. | |
| 5,907,872 A | 6/1999 | Alberts et al. | |
| 5,921,974 A | 7/1999 | Kikuchi | |
| 5,953,754 A | 9/1999 | Rosch et al. | |
| 5,956,774 A | 9/1999 | Mackley | |
| 5,978,971 A | 11/1999 | Wald | |
| D417,940 S | 12/1999 | Coates et al. | |
| 6,009,558 A | 1/2000 | Rosch et al. | |
| 6,010,586 A | 1/2000 | Suprise | |
| 6,018,822 A | 2/2000 | Hernandez | |
| 6,022,443 A | 2/2000 | Rajala et al. | |

| | | | | | |
|---|---|---|---|---|---|
| 6,105,171 A | 8/2000 | Niedermeyer | EP | 1 118 277 | 7/2001 |
| 6,115,847 A * | 9/2000 | Rosch et al. ............... 2/238 | EP | 1 125 571 | 8/2001 |
| 6,142,983 A | 11/2000 | Suprise et al. | EP | 1 159 883 | 12/2001 |
| 6,145,132 A | 11/2000 | Towner | EP | 1 166 730 | 1/2002 |
| 6,149,637 A | 11/2000 | Allen et al. | EP | 1 179 302 | 2/2002 |
| 6,149,755 A | 11/2000 | McNichols et al. | EP | 1 184 012 | 3/2002 |
| 6,168,585 B1 | 1/2001 | Cesco-Cancian | EP | 1 188 427 | 3/2002 |
| 6,174,303 B1 | 1/2001 | Suprise et al. | FR | 1.276.791 | 10/1960 |
| 6,192,521 B1 | 2/2001 | Alberts et al. | GB | 238557 | 8/1926 |
| 6,205,592 B1 | 3/2001 | Gouws | GB | 307652 | 3/1929 |
| 6,248,097 B1 | 6/2001 | Beitz et al. | GB | 571098 | 8/1945 |
| 6,287,169 B1 | 9/2001 | Willms et al. | GB | 620555 | 3/1949 |
| 6,289,519 B1 | 9/2001 | Murakami et al. | GB | 701081 | 12/1953 |
| 6,293,934 B1 | 9/2001 | Kumasaka | GB | 1342022 | 12/1973 |
| 6,293,936 B1 | 9/2001 | Otsubo | GB | 2069820 | 9/1981 |
| 6,293,937 B2 | 9/2001 | Matsushita et al. | GB | 2112268 | 7/1983 |
| 6,308,339 B1 | 10/2001 | Murakami et al. | GB | 2196525 | 5/1988 |
| 6,312,420 B1 | 11/2001 | Sasaki et al. | GB | 2 208 263 | 3/1989 |
| 6,319,347 B1 | 11/2001 | Rajala et al. | GB | 2269978 | 3/1994 |
| 6,342,050 B1 | 1/2002 | Rönnberg et al. | GB | 2269998 | 3/1994 |
| 6,368,312 B1 | 4/2002 | Otsubo | GB | 2269999 | 3/1994 |
| D456,995 S | 5/2002 | Baker | GB | 2327859 | 2/1999 |
| 6,463,591 B1 | 10/2002 | Toratani | JP | 04-242643 | 8/1992 |
| 6,475,201 B2 | 11/2002 | Saito et al. | JP | 2000 093462 | 4/2000 |
| 6,513,221 B2 | 2/2003 | Vogt et al. | JP | 2000 355690 | 12/2000 |
| 6,516,473 B2 | 2/2003 | Saito | JP | 2001 172801 | 6/2001 |
| 6,539,554 B1 | 4/2003 | Portela | JP | 2001 172802 | 6/2001 |
| 6,560,786 B2 | 5/2003 | Lipton | JP | 3177341 | 6/2001 |
| 6,562,167 B2 | 5/2003 | Coenen et al. | JP | 2001 204762 | 7/2001 |
| 6,565,691 B2 | 5/2003 | Tomsovic et al. | JP | 2001 204764 | 7/2001 |
| 6,585,840 B2 | 7/2003 | Rabe et al. | JP | 2001 204765 | 7/2001 |
| 6,596,113 B2 | 7/2003 | Csida et al. | JP | 3182069 | 7/2001 |
| 6,610,901 B2 | 8/2003 | McMahon-Ayerst et al. | JP | 2001 207301 | 8/2001 |
| 6,626,883 B2 | 9/2003 | Wada et al. | JP | 2001 224615 | 8/2001 |
| 6,666,851 B2 | 12/2003 | Otsubo et al. | JP | 2001 238909 | 9/2001 |
| 6,723,034 B2 | 4/2004 | Durrance et al. | JP | 2001 245929 | 9/2001 |
| 807,685 A1 | 10/2004 | Hasegawa et al. | JP | 2001 248002 | 9/2001 |
| 2001/0014798 A1 | 8/2001 | Fernfors | JP | 2001 254202 | 9/2001 |
| 2001/0044614 A1 | 11/2001 | Damay et al. | JP | 2001 262402 | 9/2001 |
| 2002/0000291 A1 | 1/2002 | Coenen et al. | JP | 3205643 | 9/2001 |
| 2002/0002021 A1 | 1/2002 | May et al. | JP | 3205690 | 9/2001 |
| 2002/0002358 A1 | 1/2002 | Durrance et al. | JP | 3208258 | 9/2001 |
| 2002/0009940 A1 | 1/2002 | May et al. | JP | 2001 299813 | 10/2001 |
| 2002/0084017 A1 | 7/2002 | Rabe et al. | JP | 3221601 | 10/2001 |
| 2002/0087137 A1 | 7/2002 | Christoffel et al. | JP | 2001 309946 | 11/2001 |
| 2002/0099345 A1 | 7/2002 | Saito et al. | JP | 2001 333932 | 12/2001 |
| 2003/0109842 A1 | 6/2003 | Louis et al. | JP | 2002 095700 | 4/2002 |
| 2003/0115660 A1 | 6/2003 | Hopkins | JP | 2002-320641 | 11/2002 |
| 2004/0098791 A1 | 5/2004 | Faulks | JP | 2004 159949 | 6/2004 |
| 2004/0102746 A1 | 5/2004 | Mortell et al. | WO | WO 95/16421 | 6/1995 |
| 2004/0107481 A1 | 6/2004 | Mortell et al. | WO | WO 95/18589 | 7/1995 |
| 2004/0116881 A1 | 6/2004 | Nordness et al. | WO | WO 96/03950 | 2/1996 |
| | | | WO | WO 97/02797 | 1/1997 |
| | FOREIGN PATENT DOCUMENTS | | WO | WO 99/33421 | 7/1999 |
| CA | 2356510 A1 | 2/2003 | WO | WO 01/03524 | 1/2001 |
| DE | 435 579 | 2/1927 | WO | WO 01/58401 | 8/2001 |
| DE | 809 844 | 8/1951 | WO | WO 01/61093 | 8/2001 |
| DE | 839 244 | 5/1952 | WO | WO 01/67900 | 9/2001 |
| DE | 101 44 255 | 2/2003 | WO | WO 01/87217 | 11/2001 |
| EP | 0 217 032 | 4/1987 | WO | WO 01/87218 | 11/2001 |
| EP | 0 585 766 | 3/1994 | WO | WO 01/87562 | 11/2001 |
| EP | 0 717 971 | 6/1996 | WO | WO 01/87753 | 11/2001 |
| EP | 0 763 353 | 3/1997 | WO | WO 01/88245 | 11/2001 |
| EP | 0 549 988 | 6/1998 | WO | WO 02/49565 | 6/2002 |
| EP | 0 904 758 | 3/1999 | WO | WO 02/052967 | 7/2002 |
| EP | 0 911 006 | 4/1999 | WO | WO 03/041625 A1 | 5/2003 |
| EP | 0 925 729 | 6/1999 | WO | WO 03/057107 | 7/2003 |
| EP | 0 933 072 | 8/1999 | WO | WO 2004/062398 | 7/2004 |
| EP | 1 048 231 | 11/2000 | WO | WO 2004/073430 A2 | 9/2004 |
| EP | 1 060 677 | 12/2000 | | | |
| EP | 1 060 679 | 12/2000 | | OTHER PUBLICATIONS | |
| EP | 1 108 371 | 6/2001 | | | |
| EP | 1 108 372 | 6/2001 | US 5,915,536, 06/1999, Alberts et al. (withdrawn) | | |
| EP | 1 108 373 | 6/2001 | | | |
| EP | 1 110 463 | 6/2001 | * cited by examiner | | |

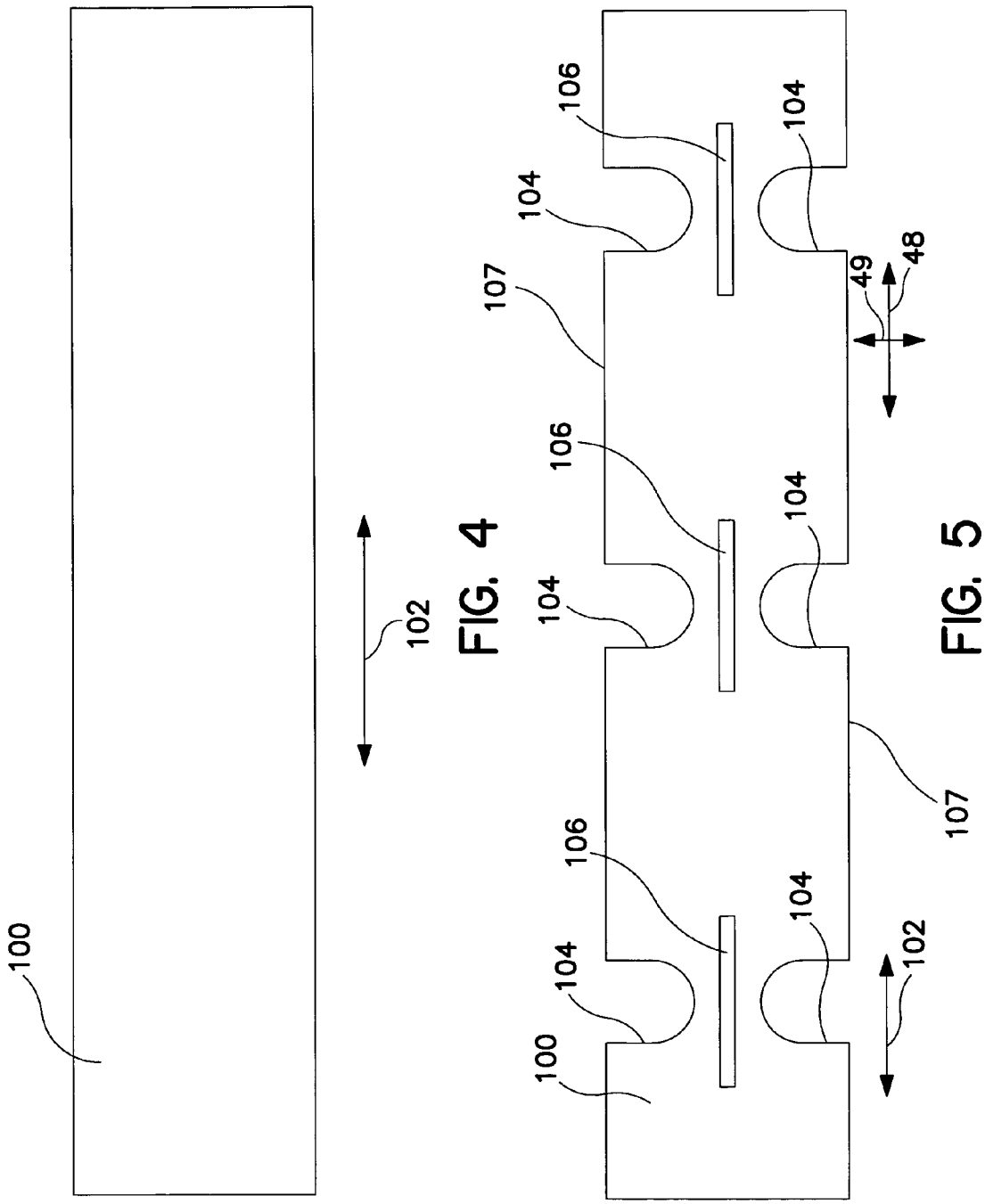

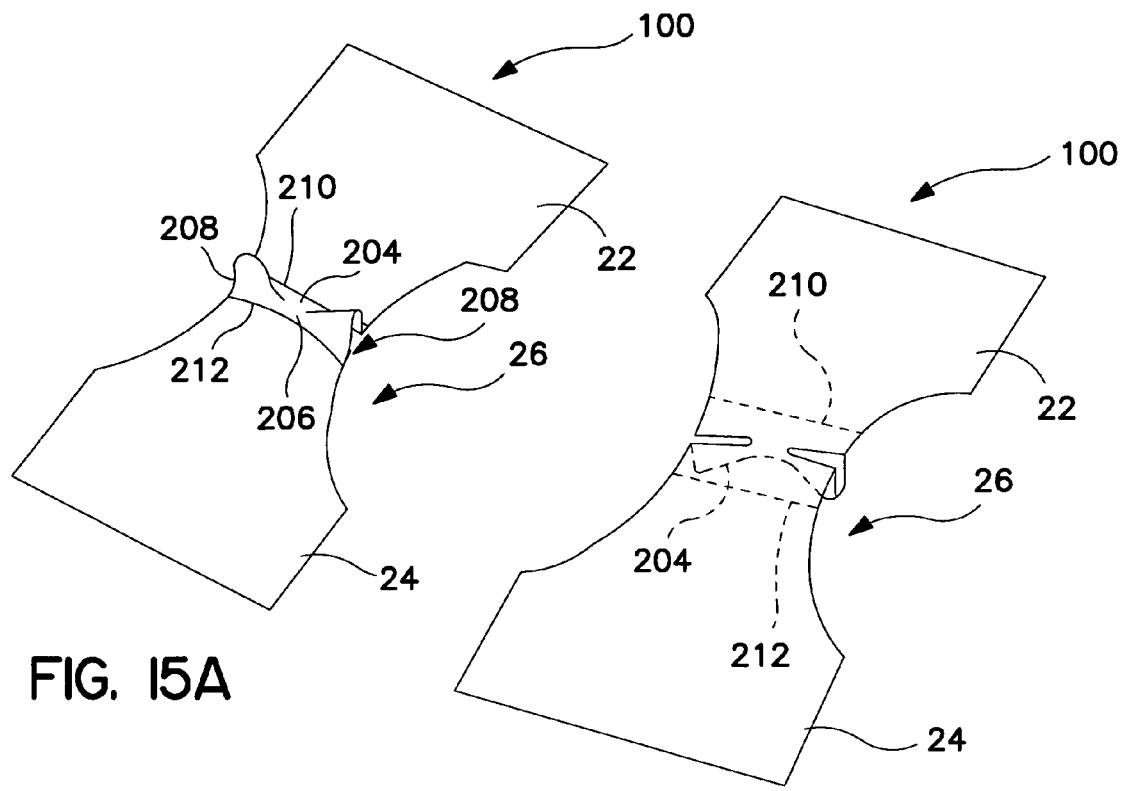
FIG. 15A
FIG. 15B
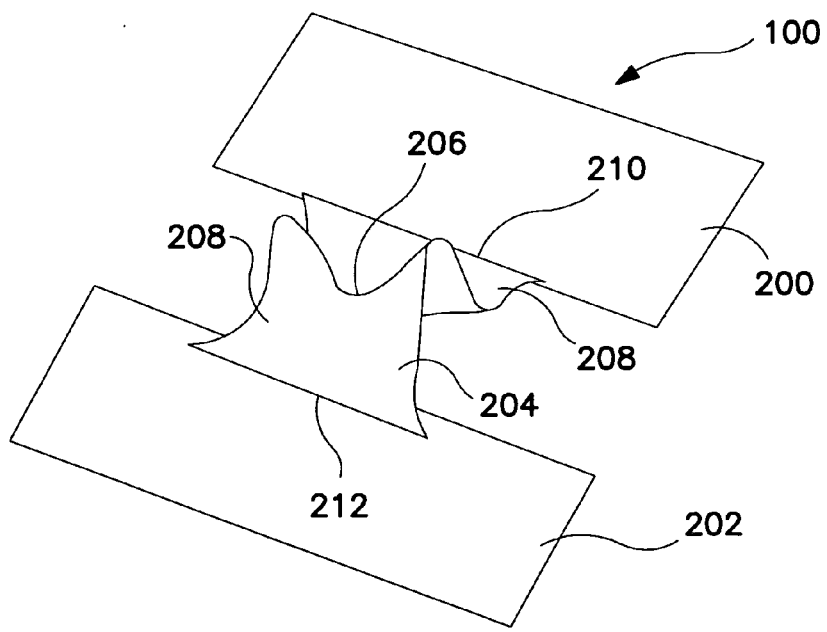
FIG. 15C

US 8,176,573 B2

BOXER SHORTS AND PROCESS OF MAKING BOXER SHORTS FROM ONE OR MORE WEBS

RELATED APPLICATION

This application is a continuation-in-part of U.S. patent application Ser. No. 10/314,915, filed 9 Dec. 2002 now abandoned. The disclosure of the prior application is incorporated herein by reference.

BACKGROUND OF THE INVENTION

This invention is directed to pants and methods of making pants having side seams and hanging legs. The boxer shorts may be absorbent or non-absorbent.

Pant-like garments have numerous applications including disposable clothing, training pants, feminine care products, adult incontinence products, disposable swimwear, or the like. Pant-like disposable garments are typically three-dimensional products with closed sides so that the product has a unitary waist opening and two leg openings. The wearer raises and lowers the garment to apply the product. Three-dimensional, boxer shorts-like products are particularly appealing because the boxer shorts look more like conventional articles of clothing than other types of disposable absorbent articles.

Many disposable pants are formed as composite structures in which several components are combined to form a product specifically suited to its intended purpose. For example, disposable pants often include one or more absorbent materials intended to absorb various bodily exudates such as urine, menstrual fluid, and/or sweat. Such products may include a liquid permeable bodyside liner and a liquid impermeable outer cover, and can include other materials and features such as elastic materials and containment structures.

However, many disposable pants are aesthetically unappealing. Existing disposable absorbent pants can be overly bulky and often resemble disposable baby diapers. Various attempts have been made to provide disposable pants having an improved, more clothing-like appearance. However, disposable pants, particularly disposable absorbent boxer shorts, present many manufacturing challenges. In part, this is due to the high speed that is necessary to economically produce relatively low-cost disposable absorbent products. Product design is often compromised by cost and manufacturing constraints, resulting in disposable pants that lack aesthetic appeal and product function. In addition, crotch depth is required for a good fit, but difficult to achieve in a garment like boxer shorts with hanging legs when using conventional manufacturing processes.

There is thus a need or desire for garment-like, aesthetically appealing boxer shorts, as well as methods of efficiently manufacturing such boxer shorts.

SUMMARY OF THE INVENTION

In response to the discussed difficulties and problems encountered in the prior art, new pants, and methods for manufacturing such pants, have been invented. The material for the garment shell of the pant may be handled as a single web, or a continuous web of multiple pants, throughout assembly until seaming in order to streamline the assembly. Leg extension materials may be added to the web to provide longer pant legs and/or to enhance the inner-leg fit of the garment. The pants can include an absorbent structure and can be made in either the machine direction or the cross direction.

More particularly, the pant may include a garment shell with front and back regions, a crotch region between the front and back regions, front and back waist edges, side seams connecting the front region to the back region, and two leg openings and hanging legs. Longitudinal seams between any two pieces of the web extending along all or any portion of a longitudinal centerline of the garment may not be needed.

The front, back, and crotch regions may each be part of a single web. Alternatively, the front and back regions may include separate panels connected to one another in the crotch region. Additionally or alternatively, the crotch region may include a separate panel that connects the front region to the back region. A portion of the garment shell may be cut, either as slits or as removable portions, to form two leg openings along transverse edges of the garment shell, with the leg openings defining, in part, a separation between the front region and the back region. An absorbent structure can be attached to the garment shell on the front region, the back region, and/or the crotch region. When the front, back, and/or crotch regions include separate panels, the panels may be different types of material. For example, the crotch panel may include an extensible or elastomeric material while the front and back panels may include inextensible or inelastic material.

In some embodiments, the crotch region may be separated from the front and back regions by folds. Furthermore, the crotch region may include a separate panel attached to the front and back regions. In either case, the crotch region may be stabilized along a longitudinal centerline of the garment, thereby leaving distal edges of the crotch region unencumbered and free to hang. In certain embodiments, a crotch panel may be attached to the front, back, and/or crotch regions to form a contoured shape in the crotch region. More particularly, the bonds attaching the crotch panel to the remainder of the web, and/or the edges of the crotch panel itself, may define a bow-tie-shaped crotch panel with a central region of the crotch panel being narrower than distal regions of the crotch panel. In embodiments such as these, when the front and back regions include separate panels, the front and back panels may be at least partially bonded directly to one another beneath the crotch panel, or not bonded directly to one another at all. In any case, the garment shell may be contracted along at least a portion of a longitudinal centerline of the garment shell, but contraction is not necessary in all embodiments.

Some embodiments may include leg extensions attached to the leg openings separating the front and back regions to enhance the hanging legs. The leg extensions may be different types of material than the front and back regions. For example, the front and back regions may include an extensible or elastomeric material while the leg extensions may include inextensible or inelastic material. As another example, the leg extensions may include an extensible or elastomeric material while the front and back regions may include inextensible or inelastic material.

For example, T-shaped cuts may be made in the garment web, and two leg extension strips can be attached to the garment web, with a longitudinal edge of each leg extension strip attached along an interior longitudinal edge of one T-shaped cut and each of two transverse edges of the same strip attached along a distal longitudinal edge of the same T-shaped cut.

As another example, both leg extensions in a single garment may be formed from a single leg-extension web that is cut along each of two longitudinally opposed edges of the leg-extension web. A first edge of each cut portion of the leg-extension web is attached along a first leg opening of the garment shell and a second edge of each cut portion of the leg-extension web is attached along a second leg opening of the garment shell. The garment shell may be a single web, or may include separate front and back regions. When the garment shell includes separate front and back regions, the first edge of each cut portion of the leg-extension web is attached along one edge of the front region and the second edge of each cut portion of the leg-extension web is attached along one edge of the back region, and the edges of the front and back regions define the leg openings.

As yet another example, a leg-extension web may be formed into a tube, which is then partially cut along a circumference of the tube, leaving an uncut crotch portion that connects the two resulting pant legs. The two pant legs can then be attached to the front and back regions with the crotch portion of the tube connecting the front and back regions.

The invention relates to a wide variety of absorbent and non-absorbent pants, including training pants, swim pants, diaper pants, incontinence garments, feminine care products, health care garments, apparel for institutional, industrial, and consumer use, or other garments. Disposable absorbent pants are adapted to be worn adjacent to the body of a wearer to absorb and contain various exudates discharged from the body.

BRIEF DESCRIPTION OF THE DRAWINGS

These and other objects and features of this invention will be better understood from the following detailed description taken in conjunction with the drawings, wherein:

FIG. 4 is a top view of a web.

FIG. 5 is a top view of the web of FIG. 4 including leg openings and strips applied to the web for assembling pants according to one embodiment of the invention using a machine direction assembly.

FIGS. 15A-15C are perspective views of garments having contoured crotch panels.

DEFINITIONS

Figure 1:
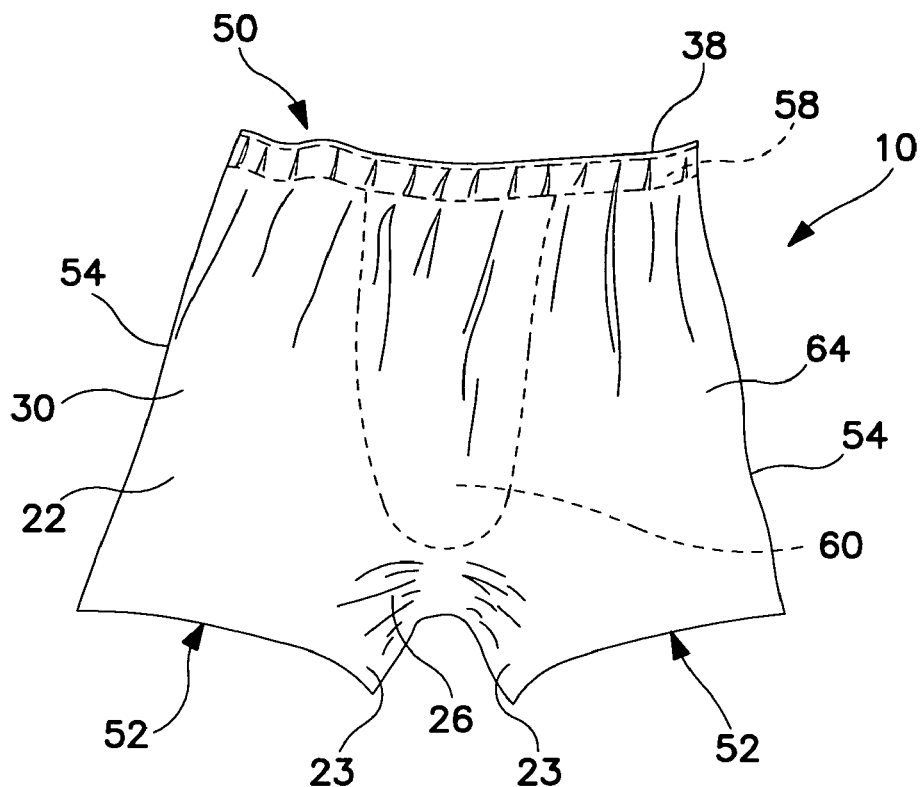
FIG. 1 is a front view of one embodiment of a pant according to the invention.

Within the context of this specification, each term or phrase below will include the following meaning or meanings.

"Attached" refers to the joining, adhering, connecting, bonding, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Boxer shorts" refers to a garment having hanging legs.

"Coform" is a composite material that is essentially an air-formed matrix of thermoplastic polymer microfibers, including meltblown fibers, and a multiplicity of individualized cellulose and/or staple fibers and/or particulates such as superabsorbents disposed throughout the matrix of microfibers and engaging at least some of the microfibers to space the microfibers to intertwine and hold captive within the matrix of microfibers by mechanical entanglement of the microfibers with the cellulose and/or staple fibers and/or particulates including superabsorbent.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Corrugated" refers to the condition of a material which has been gathered into pleats or regular rugosities or folds, the material being shortened thereby.

"Cut-out" refers to a cut portion that includes one portion of a web removed from a remainder of the web, as opposed to a "slit," which is a cut in a web that does not result in the removal of any portion of the web.

"Disposable" refers to articles which are designed to be discarded after a limited use rather than being laundered or otherwise restored for reuse.

"Distal" refers to a spatial relationship that is closer to an exterior edge or exterior surface than an interior or central location.

"Elastic," "elasticized," "elasticity," and "elastomeric" refer to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation. Conversely, "inelastic" refers to a material that is not elastomeric.

"Extensible" means that a material can be stretched, without breaking, by at least 50% (to 150% of its initial (unstretched) length) in at least one direction, suitably by at least 100% (to 200% of its initial length), desirably by at least 150% (to at least 250% of its initial length). An extensible material may or may not be elastomeric. "Inextensible" refers to a material that is not extensible.

"Fabric" is used to refer to all woven, knitted and nonwoven fibrous webs.

"Garment shell" refers to an outer cover or outer layer of a garment. In a single-ply garment, the single layer of the garment is the garment shell.

"Garment insert" refers to an inner layer of a garment. The garment insert provides a close-to-the-body fit about a wearer's lower torso, thereby serving as a form of built-in underwear within the garment.

"Hanging legs" refers to the portions of a garment which extend from the crotch region downward to the leg openings. "Downward" refers to a direction toward the ground when the garment is positioned on a standing wearer.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, while fibers having contact angles greater than 90 degrees are designated "nonwettable" or hydrophobic.

"Integral" is used to refer to various portions of a single unitary element rather than separate structures bonded to or placed with or placed near one another.

"Laid flat configuration" refers to a garment in which the side seams are not formed, or are unattached, and any elastic members are uncontracted, such that at least a majority of the garment is resting in the plane defined by the longitudinal and transverse axes without folding any portion of the garment into the defined plane. The laid flat configuration does not require the entirety of the garment to be planar, particularly since certain portions of the garment may not naturally lie within the plane without being folded or otherwise forcefully manipulated into the plane.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

Figure 3A:
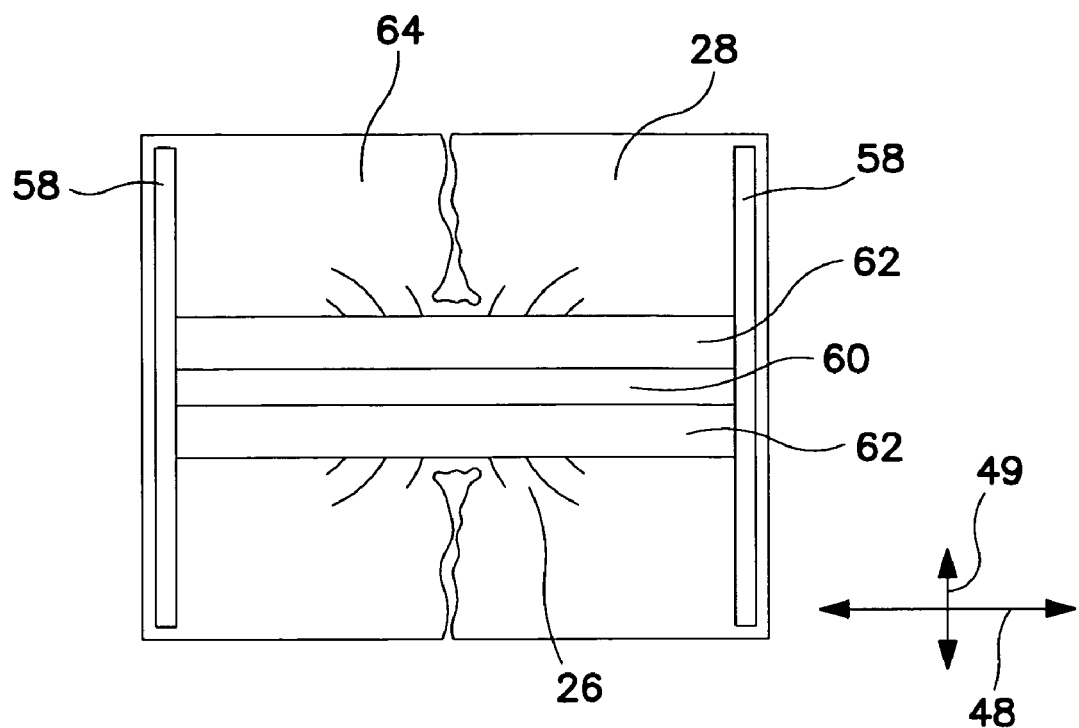
FIG. 3A is a plan view of the garment shown in FIG. 2A, showing the side facing the wearer.
Figure 3B:
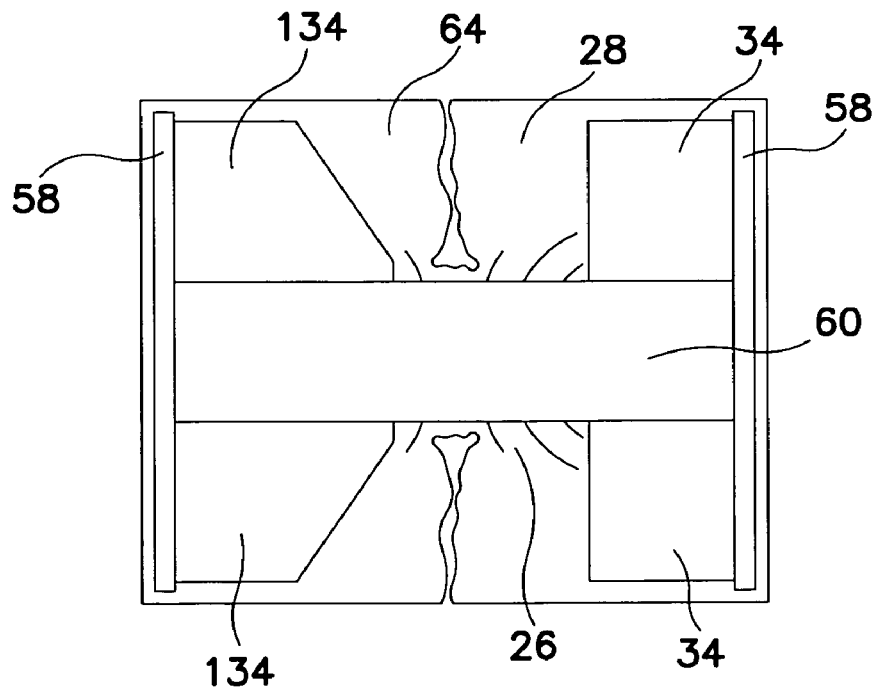
FIG. 3B is a plan view of the garment shown in FIG. 2B, showing the side facing the wearer.
Figure 3C:
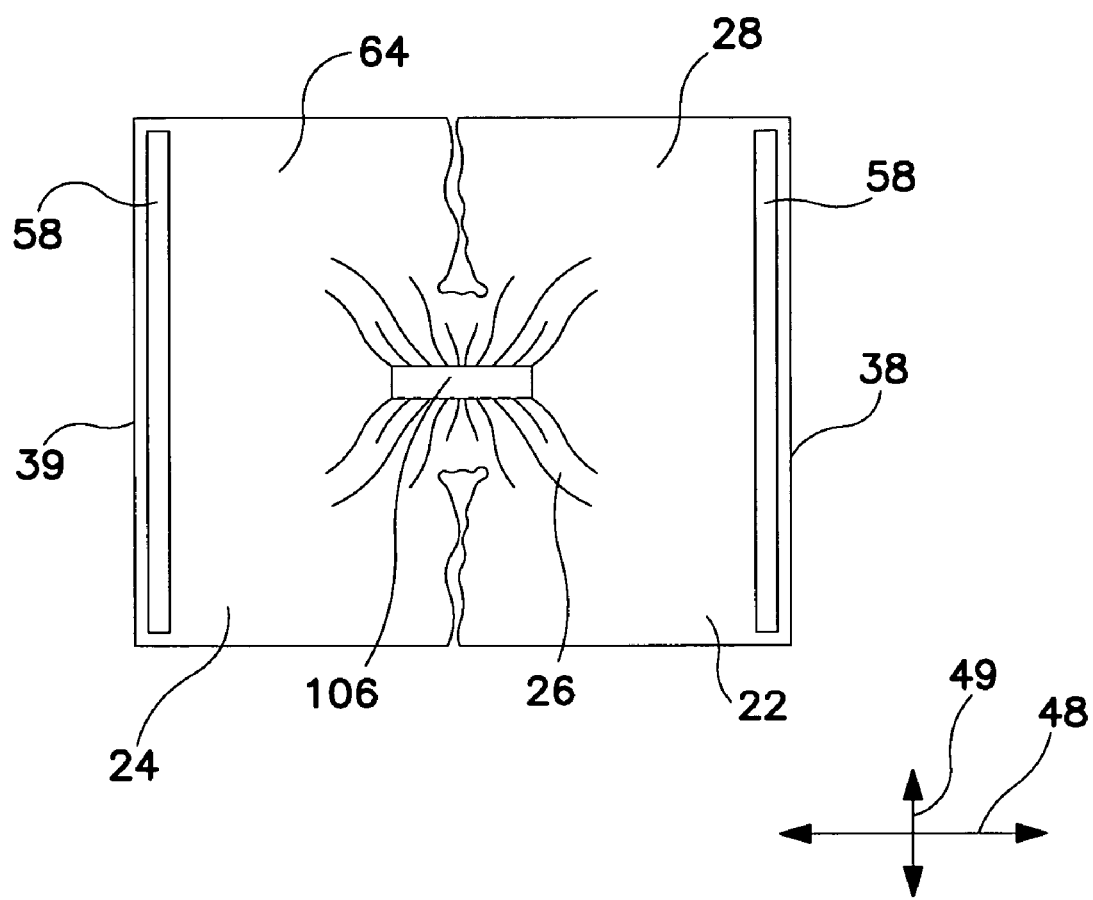
FIG. 3C is a plan view of the garment shown in FIG. 2A, showing the side facing the wearer without an absorbent structure.

"Longitudinal" and "transverse" have their customary meaning, as indicated by the longitudinal and transverse axes depicted in FIGS. 3A and 3C, and are defined with respect to the garment shell. The longitudinal axis lies in the plane of the article and is generally parallel to a vertical plane that bisects a standing wearer into left and right body halves when the article is worn. The transverse axis lies in the plane of the article generally perpendicular to the longitudinal axis.

"Machine direction" refers to the length of a fabric in the direction in which it is produced, as opposed to "cross direction" which refers to the width of a fabric in a direction generally perpendicular to the machine direction.

Figure 10:
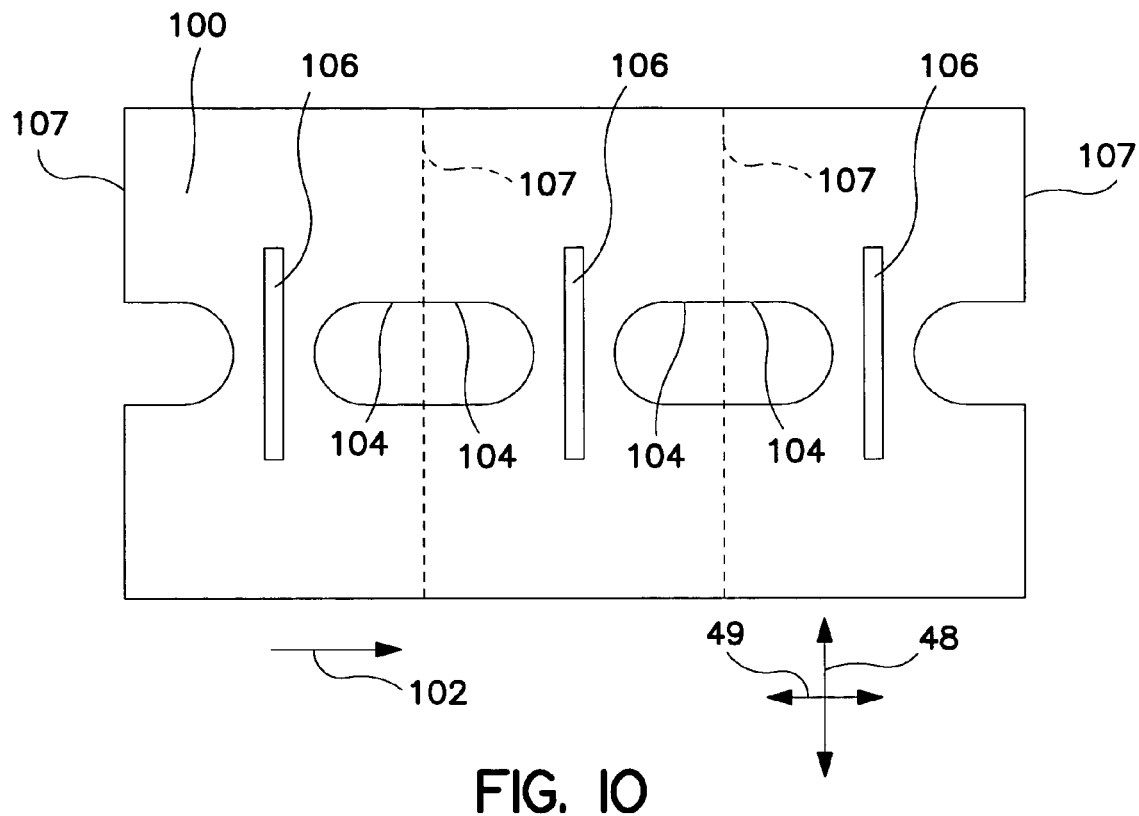
FIG. 10 is a top view of the web of FIG. 4 including leg openings and strips applied to the web for assembling pants according to one embodiment of the invention using a cross direction assembly.

The term "machine direction assembly" refers to a manufacturing process in which disposable products travel in an end-to-end or waist-to-waist orientation, in the longitudinal direction shown by arrow 48 in FIG. 5. A process utilizing a machine direction assembly entails products traveling in a machine direction through a converting machine with their longitudinal axes 48 (FIGS. 3A, 3C) parallel to the direction of arrow 102 (FIG. 5). "Cross direction assembly" entails the products traveling in a machine direction in a side-by-side orientation with their lateral axes 49 (FIGS. 3A, 3C) parallel to the direction of arrow 102, such as is illustrated in FIG. 10.

"Member" when used in the singular can have the dual meaning of a single element or a plurality of elements.

"Non-planar" refers to any portion of a garment that does not lie within the plane defined by the longitudinal axis and the transverse axis when the garment web is in a laid flat configuration.

"Nonwoven" and "nonwoven web" and "web" refer to materials and webs of material which are formed without the aid of a textile weaving or knitting process.

"Operatively joined," with reference to the attachment of an elastic member to another element, means that the elastic member can be attached to or connected to the element, and can additionally be treated with heat or chemicals, by prestretching, or the like, to give the element elastic properties; and with reference to the attachment of a non-elastic member to another element, means that the member and element can be attached in any suitable manner that permits or allows them to perform the intended or described function of the joinder. The joining, attaching, connecting or the like can be either direct, such as joining either member directly to an element, or can be indirect by means of an additional member disposed between the member and the element.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

"Surface" includes any layer, film, woven, nonwoven, laminate, composite, or the like, whether pervious or impervious to air, gas, and/or liquids.

"Three-dimensional garment" refers to a garment that cannot be laid flat with all of its seams in one plane.

These terms may be defined with additional language in the remaining portions of the specification.

DESCRIPTION OF PREFERRED EMBODIMENTS

Figure 2A:
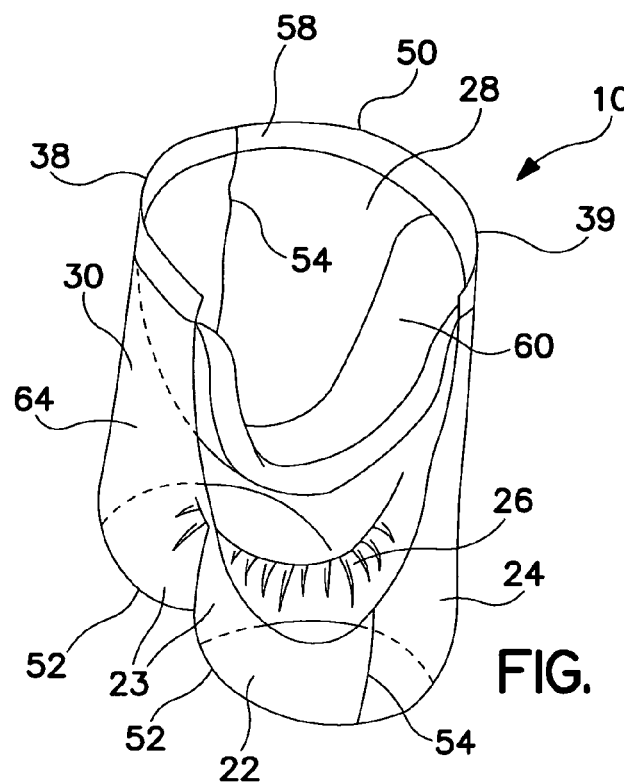
FIG. 2A is a perspective cut-away view of one embodiment of a pant according to the invention.
Figure 2B:
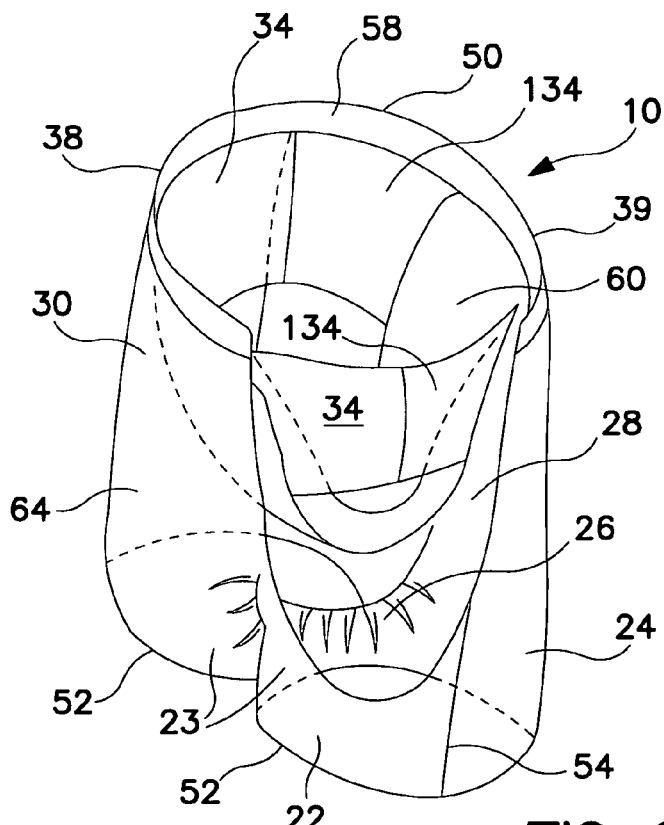
FIG. 2B is a perspective cut-away view of one embodiment of a pant according to the invention.

As representatively illustrated in FIGS. 1, 2A, and 2B, an embodiment of a pant 10 of the invention includes a garment shell 64. The garment shell 64 can include a front region 22, a back region 24, a crotch region 26, an inner surface 28 which is configured to contact the wearer, and an outer surface 30 opposite the inner surface 28 which is configured to contact the wearer's clothing. The pant 10 also defines a pair of longitudinally opposed waist edges, which are designated front waist edge 38 and back waist edge 39. The front region 22 is contiguous with the front waist edge 38, and the back region 24 is contiguous with the back waist edge 39. The front region 22 includes the portion of the pant 10 which, when worn, is positioned on the front of the wearer while the back region 24 includes the portion of the pant 10 which, when worn, is positioned on the back of the wearer. The crotch region 26 of the pant 10 includes the portion of the pant which, when worn, is positioned between the legs of the wearer and covers the lower torso of the wearer. As illustrated in FIGS. 1, 2A, and 2B the front and back regions 22 and 24 are joined together at side seams 54 to define a three-dimensional pant configuration having a waist opening 50 and a pair of leg openings 52. In particular embodiments, the pant 10 can include an absorbent structure 60.

The crotch region 26 may be contracted along a longitudinal axis 48 to provide a longitudinal force. As described more fully below, the contraction of the crotch region 26 can be accomplished either elastically or inelastically. A contracted crotch region 26 provides crotch depth that provides a good fit through the crotch region 26, thereby allowing the front and back regions to hang properly. The garment shell 64 can also include hanging legs 23 which extend from the crotch region 26 downward to the leg openings 52 (FIGS. 1, 2A, and 2B).

The pant 10 also includes side seams 54 that connect the front region 22 to the back region 24 to create the pant 10. The side seams 54 can take any number of forms, including both refastenable and non-refastenable seams, as are known in the art. The provision of the side seams 54 can be accomplished in the manner described in U.S. Pat. No. 6,192,521 issued 27 Feb. 2001 to Alberts et al.; U.S. Pat. No. 5,046,272, issued 10 Sep. 1991 to Vogt et al., which is incorporated herein by reference, or in the manner described in U.S. Pat. No. 6,565, 691, issued 20 May 2003 to Tomsovic, et al.; U.S. Pat. No. 6,723,034 issued 20 Apr. 2004 to Durrance, et al.; U.S. Pat. No. 6,596,113 issued 22 Jul. 2003 to Csida, et al.; and/or U.S. Pat. No. 6,513,221 issued 4 Feb. 2003 to Vogt, et al.; all of which are incorporated herein by reference. As is known in the art, the side seams 54 can be inward or outward fin seams or lap seams (not shown).

The pant 10 can also have a waist elastic member 58 extending along at least a portion of the front waist edge 38 and/or the back waist edge 39. The waist elastic member 58 can be formed of any suitable elastic material. As is well known to those skilled in the art, suitable elastic materials include sheets, strands, or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the waist elastic member 58 includes a plurality of dry-spun coalesced multifilament spandex elastomeric threads sold under the trade name LYCRA® and available from Invista Corporation, Wilmington, Del., U.S.A. Alternatively, multiple strands of 310 decitex LYCRA® may also be laminated at 250% elongation between spunbond facings in addition to an adhesive.

As another alternative, the waist elastic member 58 can be a material exhibiting delayed retraction, or can in fact be non-elastic. Delayed retraction materials may include those designed to retract relatively slowly following compression, such as "temporarily inhibited" elastic materials. "Temporarily inhibited" materials are described, for example, in U.S. Pat. No. 5,545,158 issued Aug. 13, 1996, to Jessup, U.S. Pat. No. 5,669,996 issued Sep. 23, 1997, to Jessup, and U.S. Pat. No. 5,500,063 issued Mar. 19, 1996, to Jessup, all of which are herein incorporated by reference, and references cited therein. Alternatively, a delayed retraction material may be designed to resist retraction until an activation process occurs, such as so-called "latent elastic" materials. Suitable retractive materials for use as a delayed retraction material can alternatively comprise any material adapted to retract upon activation, whether immediately upon activation or subsequently thereto. The retractive material may include elastomeric or nonelastomeric materials. Suitable nonelastomeric retractive materials may include without limitation polyether block amides (PEBAX®) or the like, and laminates thereof. Suitable elastomeric retractive materials may include without limitation LYCRA® materials, elastomeric materials including latex or rubber or synthetic urethanes, or the like, and laminates thereof. In particular embodiments, the retractive material may include an elastomeric material having an unstable state relative to some other stable and elastic state. In such embodiments, the retractive material can, but need not, have elastomeric properties in the unstable state. Other examples include heat-shrinkable elastic materials such as described in U.S. Pat. No. 4,816,094 issued Mar. 28, 1989 to Pomplun et al., U.S. Pat. No. 4,665,306 issued May 12, 1987 to Roland et al., and U.S. Pat. No. 4,663,106 issued May 5, 1987 to Pomplun et al., all of which are herein incorporated by reference.

A pant of this type can be designed to fit wearers in a wide range of sizes by adjusting the pant dimensions based on the anthropometric features of an intended wearer. Ratios of wearer dimensions to pant dimensions for a suitable boxer-style pant have been determined and are shown in Table 1. In addition, stylistic variations such as hip-hugging (low rise), relatively more closely or loosely fitted shorts, and other styles, may be provided by varying the ratios listed in Table 1 within (or even beyond) the ranges shown. Moreover, the use of elastomeric or extensible material to form the garment shell may provide additional adaptability to fit a wider range of wearer sizes.

Figures 1A, 1B:
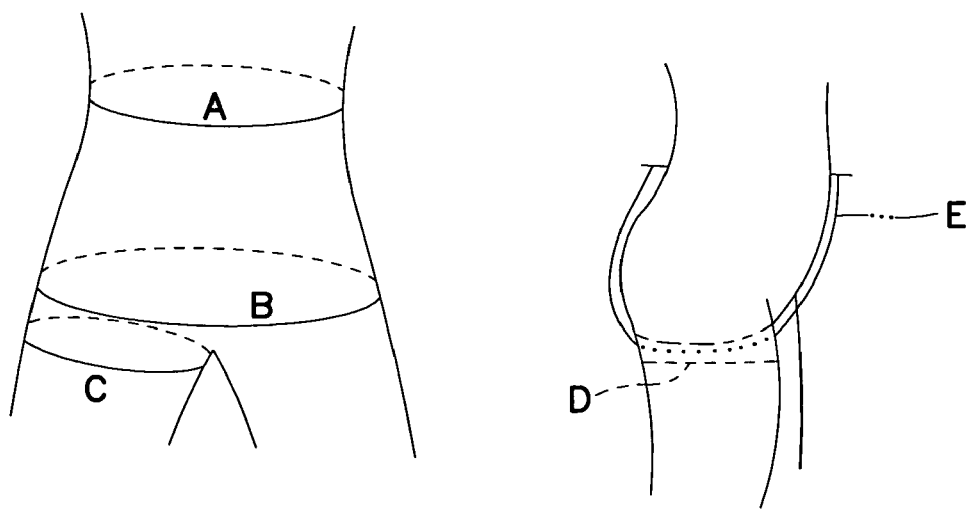
FIGS. 1A and 1B illustrate dimensions described with respect to Tables 1 and 2.

Since the pant dimensions are determined by the dimensions of the intended wearer, the ratios shown are based upon five measurements of an intended wearer, abbreviated as follows:

A: waist circumference (FIG. 1A)
B: hip circumference (FIG. 1A)
C: thigh circumference (measured in crotch region, horizontally; see FIG. 1A)
D: crotch depth (measured in crotch region, viewed 18 inches from the wearer's side; see FIG. 1B)

E: center front waist to center back waist through crotch; see FIG. 1B

Figures 5A, 5B:
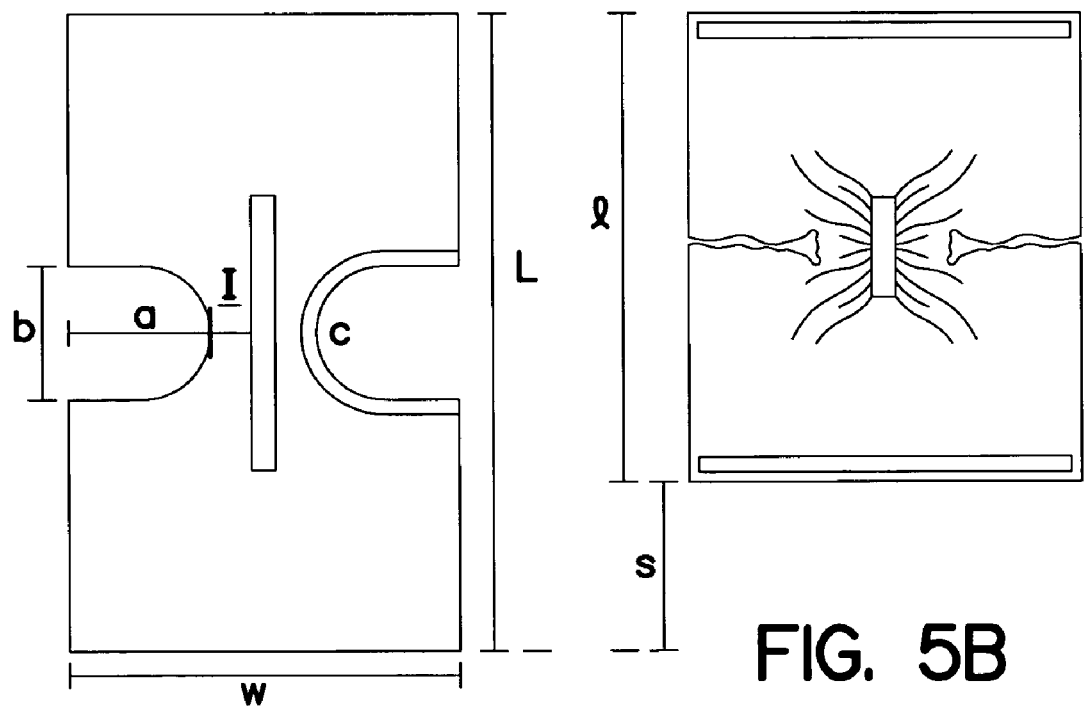
FIGS. 5A and 5B illustrate dimensions described with respect to Tables 1 and 2.

Table 2 shows how garment shell dimensions shown in FIGS. 5A and 5B are determined using body measurements A-E and ratios in Table 1. Table 2 also shows how the ratios in Table 1 have been applied to create shorts for two different size wearers, one a mannequin of a child (Wearer #1) weighing approximately 32 to 40 pounds (15-18 Kg), the other an adult female (Wearer #2) weighing approximately 125 pounds (57 Kg).

TABLE 1

| PANT DIMENSIONS | DETAILS and RATIOS | EXEMPLARY RANGES |
|---|---|---|
| Garment inseam I (FIG. 5A, dimension "I") | Selected based on garment style. There is not a seam at this location; this is simply the location where an "inseam" measurement is generally taken. After contraction, this dimension "I" provides the "hanging legs" feature of the pant. | 1–5 inches, or more |
| Width of garment shell (FIG. 5A, dimension "w") | Ratio of 2 × Width (i.e., garment circumference) to the larger of wearer's Hip or Waist circumference 2w:[B or A] | From about 1.2:1 to about 2:1, such as about 1.7, e.g. 2w = 1.2A or 1.2B |
| Length of base of arc (FIG. 5A, dimension "b") | Ratio of Arc base length to Wearer crotch depth b:D | From about 1:1 to about 1.5:1, such as about 1.25:1 |
| Circumference of leg opening (FIG. 5A, dimension "c") | Ratio of Leg opening to Wearer thigh circumference c:C | From about 1.1:1 to about 1.5:1, such as about 1.25:1 |
| Takeup (shortening) of garment shell on gathering of crotch (FIG. 5B, dimension "s") | Ratio of Takeup to 2 × Garment inseam length I s:2I | From about 1:1 to about 1.6:1, such as about 1.3:1 |
| Length of garment shell after gathering (FIG. 5B, dimension "l") | Ratio of Length after gathering to Wearer F to B waist thru crotch l:E | This can vary widely depending on the desired short style, but for a standard fit, from about 1.1:1 to about 1.4:1, such as about 1.25:1, e.g. l = 1.4E |
| Length of garment shell before gathering (FIG. 5A, dimension "L") | Sum of Takeup and Length of shell after gathering s + l | |
| Arc height (FIG. 5A, dimension "a") | (Width of garment shell – 2 × Garment inseam I)/2 (w – 2I)/2 | |

TABLE 2

|   | Wearer #1 | Short #1 | Wearer #2 | Short #2 |
|---|---|---|---|---|
| A | 50 cm |  | 78 cm |  |
| B | 54 cm |  | 96 cm |  |
| C | 29 cm |  | 55 cm |  |
| D | 10 cm |  | 16.5 cm |  |
| E | 41 cm |  | 61 cm |  |
| I |  | 6 cm |  | 8 cm |
| w |  | 45 cm |  | 67 cm |
| b |  | 12.5 cm |  | 20.5 cm |
| c |  | 36 cm |  | 68 cm |
| s |  | 15.5 cm |  | 21 cm |
| l |  | 50.5 cm |  | 75 cm |
| L |  | 66 cm |  | 96 cm |
| a |  | 15 cm |  | 25 cm |

The pant 10 can also include an absorbent structure 60. The absorbent structure 60 can be attached to the garment shell 64 at the front waist edge 38 and back waist edge 39, or at some point below the front waist edge 38 and back waist edge 39 on the front region 22 and back region 24. (FIGS. 2A and 2B). Alternatively, the absorbent structure 60 can be attached to the garment shell 64 in the crotch region 26. The absorbent structure 60 may be either permanently attached to the garment shell 64 or refastenably attached to the garment shell 64 to allow for replacement of the absorbent structure 60 when the absorbent structure 60 becomes soiled.

The absorbent structure 60 can be any structure that is generally compressible, conformable, non-irritating to the skin, and capable of absorbing and retaining liquids and certain body wastes. The absorbent structure 60 can be manufactured in a wide variety of sizes and shapes, from a wide variety of liquid absorbent materials commonly used in the art, and may be stretchable, non-stretchable, or elastic. For example, the absorbent structure 60 can suitably include a matrix of hydrophilic fibers, such as a web of cellulosic fluff, mixed with particles of a high-absorbency material commonly known as superabsorbent material. In a particular embodiment, the absorbent structure 60 includes a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 60 to better contain and absorb body exudates. The concentration of the superabsorbent particles can also vary through the thickness of the absorbent structure 60. Alternatively, the absorbent structure 60 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen, Inc. in Greensboro, N.C., U.S.A. Typically, a superabsorbent material is capable of absorbing at least about 15 times its weight in water, and desirably is capable of absorbing more than about 25 times its weight in water.

In one embodiment, the absorbent structure 60 includes a blend of wood pulp fluff and superabsorbent material. One preferred type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. As a general rule, the superabsorbent material is present in the absorbent structure 60 in an amount of from 0 to about 90 weight percent based on total weight of the absorbent assembly. The absorbent structure 60 suitably has a density within the range of about 0.10 to about 0.35 grams per cubic centimeter. The absorbent structure 60 may or may not be wrapped or encompassed by a suitable tissue or nonwoven wrap that may help maintain the integrity and/or shape of the absorbent assembly.

The absorbent structure 60 can also incorporate other materials that are designed primarily to receive, temporarily store, and/or transport liquid along the mutually facing surface with absorbent structure 60, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

In particular embodiments, the absorbent structure 60 is thin to provide a slim, comfortable, non-bulky pant 10. Any suitable thin absorbent structure may be used, such as for example, the thin absorbent described in WO 02/49565, published Jun. 27, 2002, by Sawyer et al., which is incorporated herein by reference.

The absorbent structure 60 can include a pair of containment flaps 62 (FIG. 3A) which are configured to provide a barrier to the transverse flow of body exudates. A flap elastic member (not shown) can be operatively joined with each containment flap 62 in any suitable manner as is well known in the art. The elasticized containment flaps 62 define an unattached edge which assumes an upright, generally perpendicular configuration to form a seal against the wearer's body. Suitable constructions and arrangements for the containment flaps 62 are generally well known to those skilled in the art and are described in U.S. Pat. No. 4,704,116 issued Nov. 3, 1987, to Enloe, which is incorporated herein by reference.

As an alternative, a pant-like garment insert could be used for the absorbent structure 60. For example, the pant-like garment insert may include a body side liner, an outer cover, and an absorbent assembly between the body side liner and the outer cover, and side panels. Examples of suitable pant-like garment inserts include a training pant, such as HUGGIES® PULL-UPS® Disposable Training Pants, or a disposable underpant, such as GOODNITES® Disposable Underpants, both manufactured by Kimberly-Clark Corporation, Neenah, Wis., U.S.A. A training pant serving as the pant-like garment insert for the absorbent structure 60 can include front side panels 34 and back side panels 134 (FIGS. 2B and 3B). The manufacture of training pants having side panels can be accomplished in the manner described in U.S. Pat. No. 6,562,167, issued 13 May 2003 to Coenen et al., which is incorporated herein by reference.

As another alternative, a pad-type absorbent could be used for the absorbent structure. The pad-type absorbent can be attached in the crotch region 26 of the pant 10. An example of a suitable pad-type absorbent is a feminine care pad such as KOTEX® Feminine Napkins, KOTEX® LIGHTDAYS® disposable panty liners, or an incontinence absorbent pad such as POISE® Feminine Guards and Pads or DEPEND® Guards for Men, all manufactured by Kimberly-Clark Corporation, Neenah, Wis., U.S.A.

For reference, arrows 48 and 49 depicting the orientation of the longitudinal axis and the transverse axis, respectively, of the garment shell 64 are illustrated in FIGS. 3A and 3C.

The garment shell 64 is suitably constructed of materials that are comfortable against the skin and non-irritating. It is contemplated that the garment shell 64 can be either disposable or durable. Both nonwoven and woven materials are contemplated for the garment shell 64. For example, the garment shell 64 for pant 10 can be selected from a wide variety of materials, including elastic, stretchable, or nonstretchable materials. The garment shell 64 can be a single layer of material or a multi-layered laminate structure. One example of a suitable material is a spunbond polypropylene nonwoven web. The garment shell 64 itself may be absorbent and, for example, may be made of those materials of which the absorbent structure 60 is made. For instance, the garment shell 64 may include a coform material with a polyethylene film on an outer surface of the garment. The garment shell 64 suitably provides a relatively cloth-like texture to the wearer.

The present invention also includes various methods for making pants from a web. Referring to FIG. 4, a single web 100 is provided moving in the direction represented by arrow 102. Alternatively, two webs that are joined at their edges to form a double-width piece (not shown) can be used for the web 100. The web 100 may be composed of any material previously described for the garment shell 64.

The method can be carried out using machine direction assembly so that arrow 102 can correspond to the longitudinal direction parallel to the longitudinal axis 48 as shown in FIG. 5 with the products connected end-to-end or waist-to-waist, or the method can be carried out using cross direction assembly so that arrow 102 can correspond to the transverse direction parallel to the transverse axis 49 as shown in FIG. 10 with the products connected side-to-side.

In both the machine direction process (FIGS. 5, 6-9) and the cross direction process (FIGS. 10-12), the web 100 is cut along each of the transversely opposed edges 107 of the web 100 to define leg openings 104 (FIGS. 5 and 10). More particularly, the leg opening 104 may be formed by slitting or die-cutting or otherwise removing a portion of the web 100 from the remainder of the web 100. The geometry of the leg opening 104 affects the overall product appearance. Examples of suitable cuts for creating leg openings 104 are illustrated in FIGS. 13A-13L.

When in a flat configuration, as illustrated in FIGS. 13A-13L, the leg openings 104 may simply be slits (FIGS. 13A-C) within the web, or either symmetrical (FIGS. 13D-I) or asymmetrical (FIGS. 13J-L) portions cut and removed from along each of the transversely opposed edges 107 of the web. Any suitable symmetrical or asymmetrical shape may be cut to form the leg openings 104. As referred to herein, the symmetry of the leg opening cut-outs is determined with respect to a transverse axis 49 through the web. Alternatively, the leg openings 104 may be formed by folding material adjacent to a slit in order to move a portion of the material out of the way.

Figure 13A:
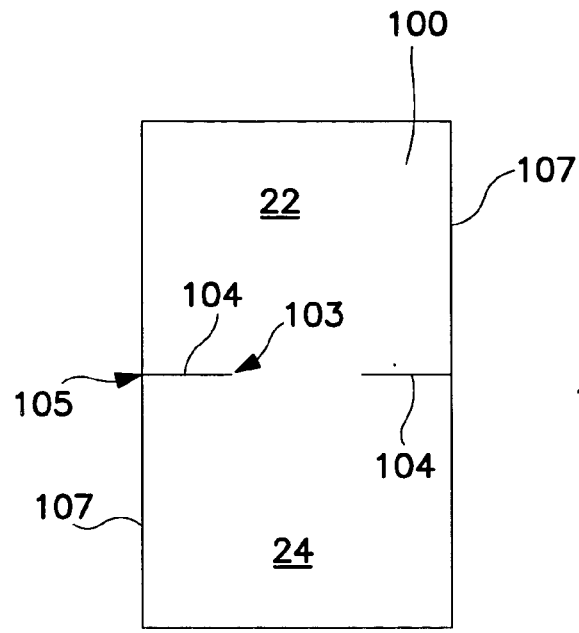
FIGS. 13A-13L are top views of the web having various leg opening embodiments.
Figure 13B:
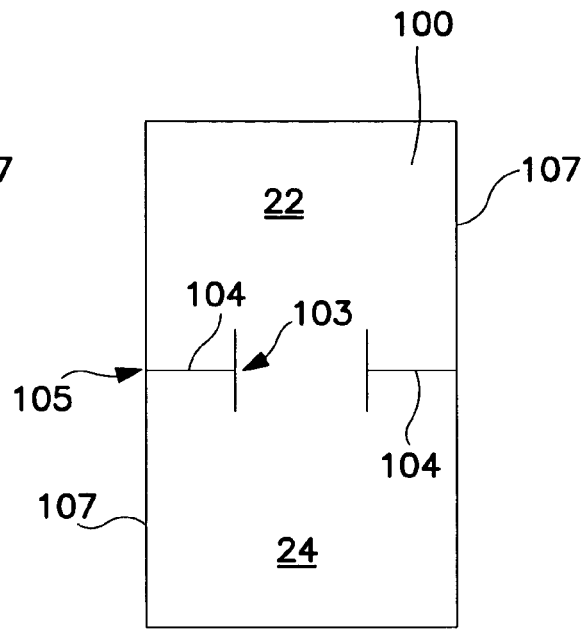

As illustrated in FIG. 13A, the leg openings 104 may be formed from single slits. Slits can result in longer legs in the garment compared to leg openings created from portions of the web that are cut out and removed from the remainder of the web. Alternatively, the leg openings 104 may be formed from T-shaped slits, as shown in FIG. 13B. Expanding the interior end 103 of the slits into a "T" shape provides pant legs that hang smoothly adjacent to the crotch region 26. Additionally, the portion of the slit extending from the interior end 103 to an open end 105 of the T-shaped slit may be hemmed along one or both edges forming this portion of the slit. Similarly, in embodiments other than T-shaped slits, a portion of the web adjacent to the cut may be folded and manipulated out of the way to create a larger leg opening 104.

Figure 13C:
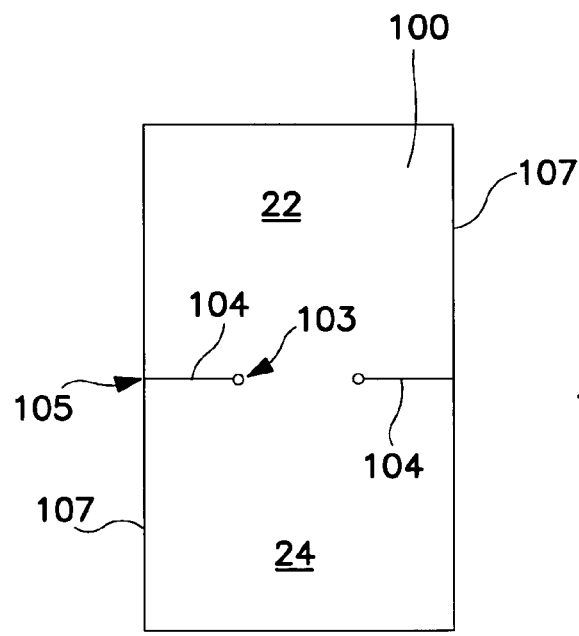

Slits may be cut using pinch-cut knives, intermittent slitters, or any other suitable straight machine-direction or cross-direction cut. Not only do the slits result in longer legs on the garment, but less web 100 material waste accrues than in the cut-out embodiments. The slits may be reinforced or otherwise adapted at the shaped interior ends 103 of the leg openings, as shown in FIG. 13C and described in further detail below. As another alternative, the slits need not initially extend all the way to the transverse edges 107 of the web, but instead may be cut within the web for easier handling of the web during the pant-forming process, and may or may not be cut at the transverse edges 107 of the web later during the pant-forming process.

Figure 13D:
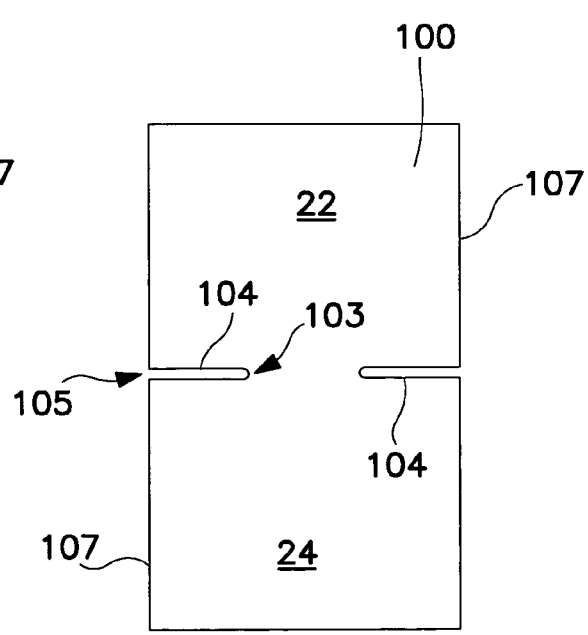
Figure 13E:
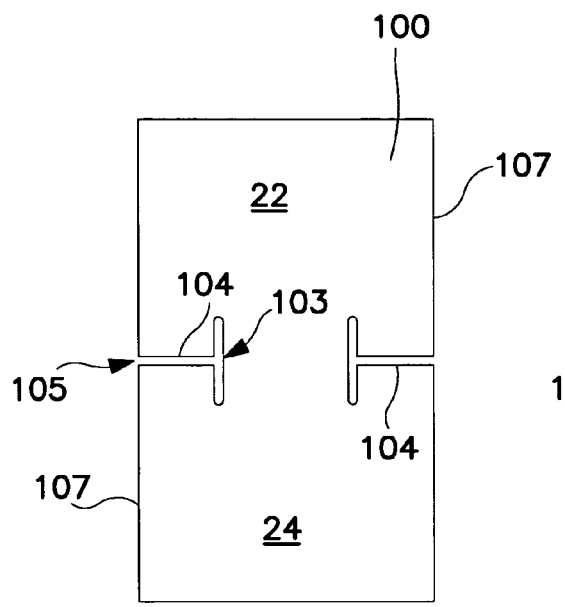
Figure 13F:
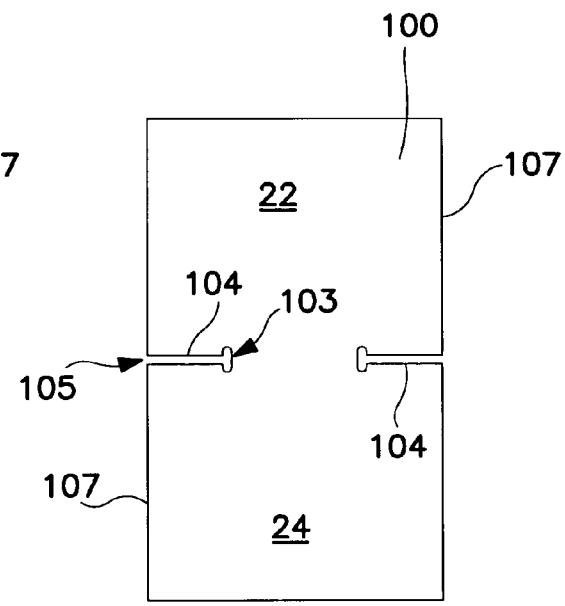

Alternatively, rather than slits, the leg openings 104 may be formed from slots, which as used herein refer to cut-outs that resemble the shape of slits but with at least some portion of the web 100 removed from the remainder of the web. The slots may be symmetrical, as illustrated in FIGS. 13D-F, or asymmetrical, as illustrated in FIG. 13J. More particularly, the slots may form substantially straight lines, as shown in FIGS. 13D and 13J, or T-shaped slots, as shown in FIG. 13E, or a slot having a reinforced interior end 103 resembling a hairpin shape, as shown in FIG. 13F.

Figure 13G:
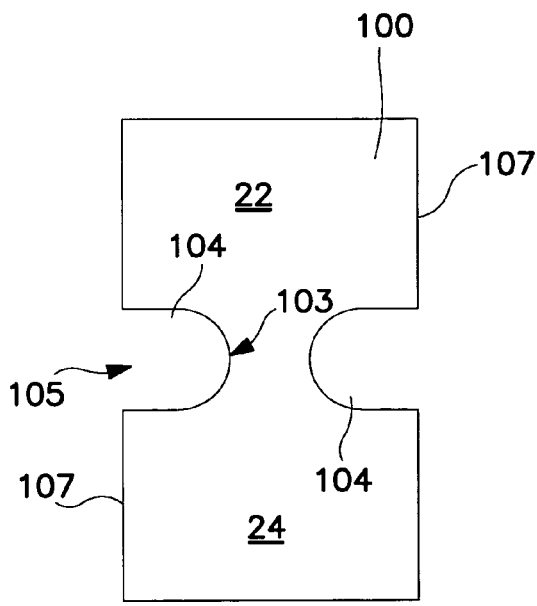
Figure 13H:
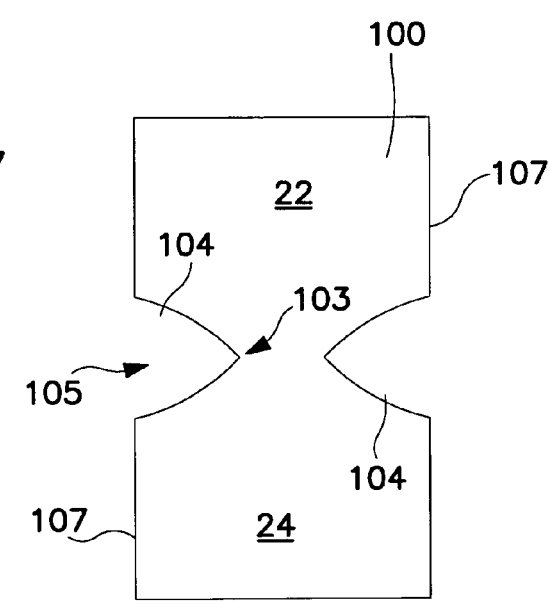

Other suitable symmetrical shapes that may be cut and removed from the web 100 to form the leg openings 104 include a "U" shape, as illustrated in FIG. 13G, as well as a "mound" shape, as illustrated in FIG. 13H. The U-shaped leg opening 104 results in relatively short garments legs, whereas mound-shaped leg openings 104 provide more body coverage than the U-shaped leg openings 104. The term "mound-shaped" refers to a cut-out portion having an angle at the interior end 103 that is less than 180 degrees, thereby resulting in a leg opening 104 having a triangular shape, or a softened triangular shape that may resemble the shape of a mound or a mountain.

Figure 13I:
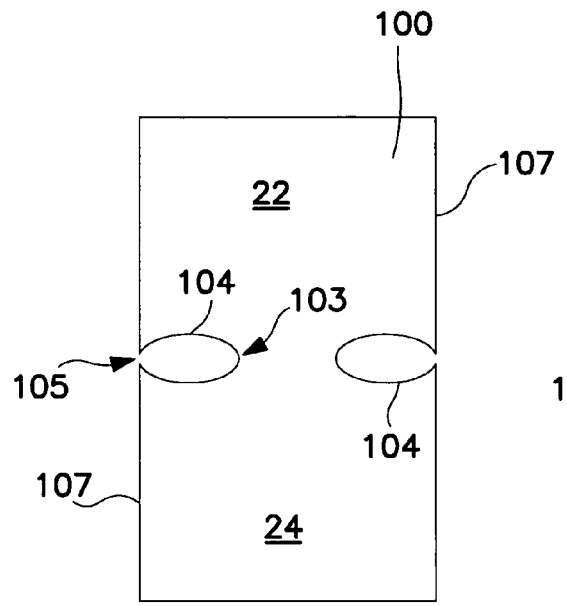
Figure 13J:
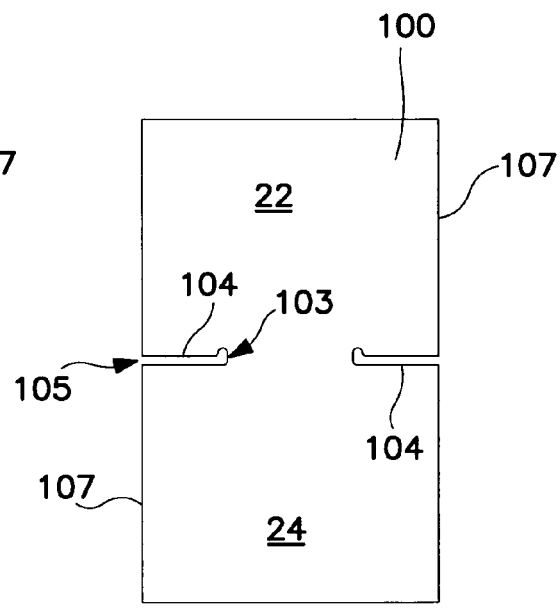
Figure 13K:
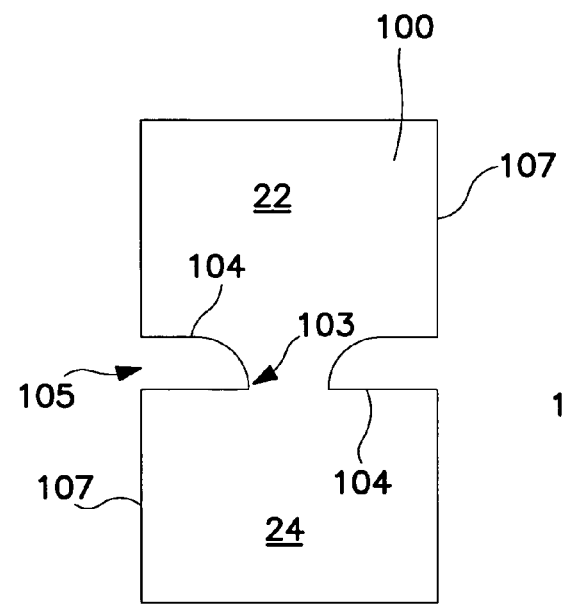
Figure 13L:
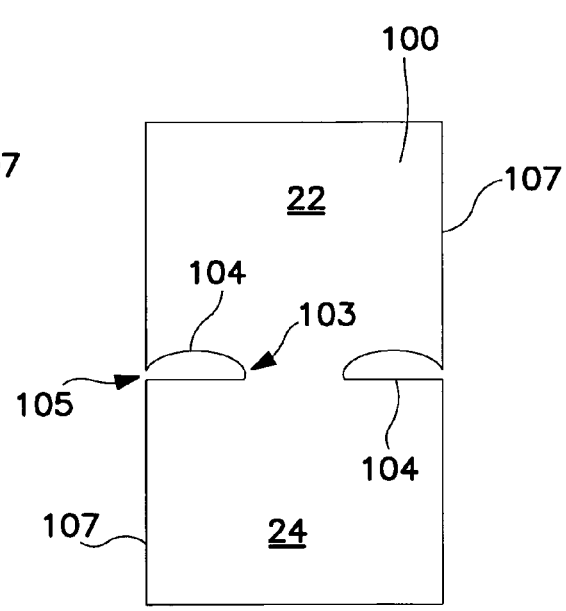

Rather than expanding from the interior end 103 of the leg opening 104 to the open end 105 of the leg opening, the leg openings 104 may be tapered at the open ends 105, thereby resulting in a teardrop shape. The tapered shape can provide a straight horizontal appearance along the leg ends of the garment even though the crotch region 26, when contracted 120, distorts the lower region of the garment. The tapered shape may be either symmetrical, as illustrated in FIG. 13I, or asymmetrical, as illustrated in FIG. 13L.

As an alternative to slits and/or symmetrical cut-outs, the leg openings 104 may be any suitable asymmetrical shape. For example, as shown in FIG. 13K, the leg openings 104 may include a straight edge along the front edge of the cut-out and a curvilinear edge along a back edge of the cut-out. This asymmetrical design provides greater butt coverage in the back of the garment and longer legs in the front of the garment.

Many of the shapes of the leg openings 104 may be reinforced by cutting a circular cut-out at the interior end 103 of the leg openings 104 to reduce stress concentration at the interior end of the openings, thereby reducing the likelihood of tearing in the crotch region 26. An example of this type of reinforcing cut-out is illustrated in FIG. 13C. The reinforcing cut-out may be other suitable shapes besides circular. For example, when the leg openings 104 are formed from slots, the reinforcing cut-out may have a shape that is wider than the longitudinal opening of the slot and narrower than the transverse opening of the slot to reduce the stress concentration. A suitable shape may be circular or oblong, as illustrated in FIG. 13F.

As more fully described below, the leg openings 104 become the leg openings 52 of the pant 10.

In the machine direction process (FIGS. 5, 6-9), strips 106 may be applied to selected areas located between the leg openings 104. Strips 106 can include elastic or non-elastic material. Examples of suitable non-elastic material include heat contractible materials, such as heat shrinkable films, for example, films formed of polyether block amides (PEBAX®, available from the Atofina Company of France) or the like. If the strips 106 are elastic, the elastic can be formed of any suitable material previously described for the waist elastic member 58. As an alternative, strips 106 can include any of the previously described delayed retraction materials.

Figure 7:
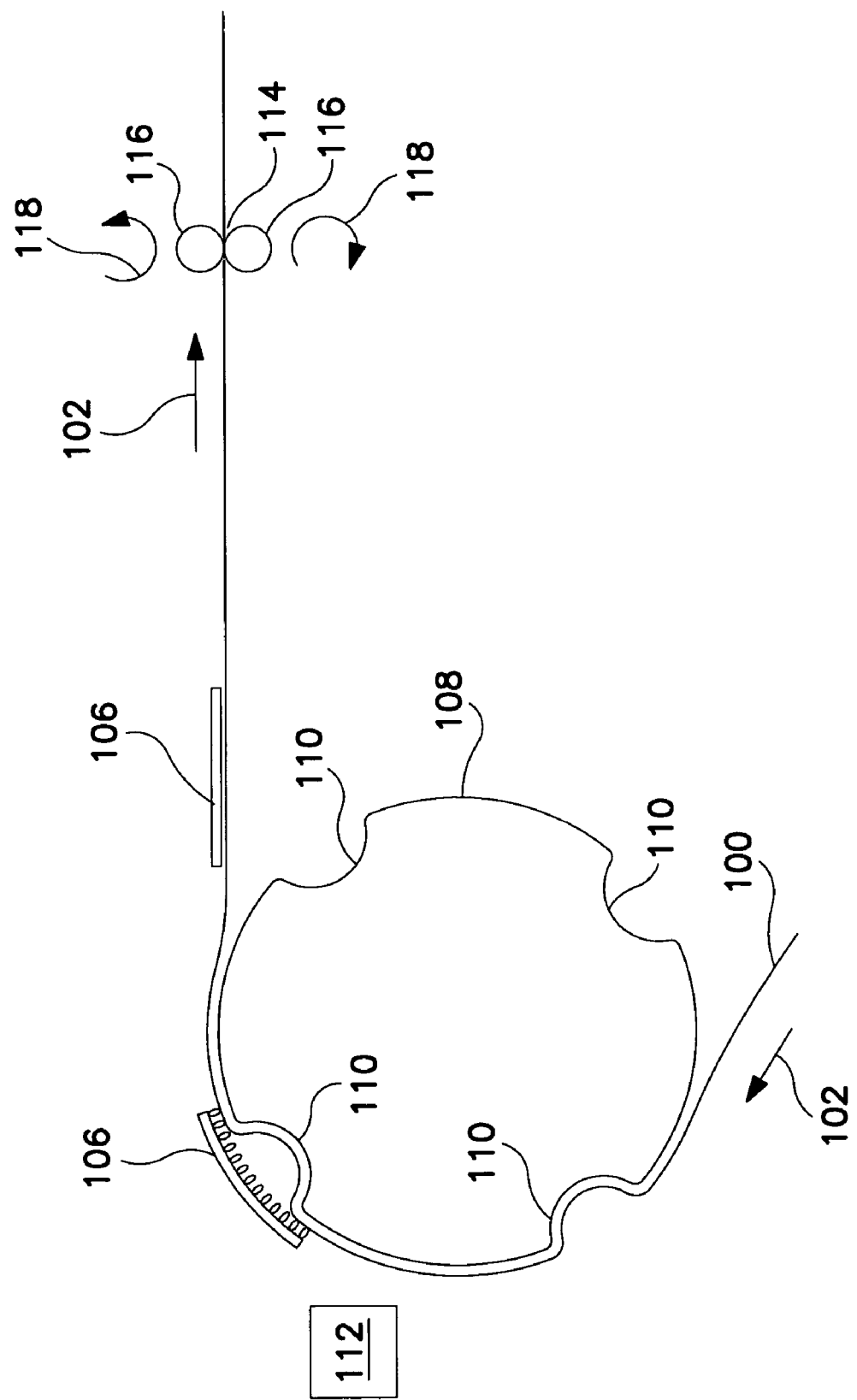
FIG. 7 is a side view of a looper drum for applying an elastic strip to the web.

Referring to FIG. 7, if the strips 106 are elastic, the strips 106 can be applied to the web 100 using a looper drum 108. Looper drums like looper drum 108 are known and are described, for example, in U.S. Pat. No. 5,171,388 issued Dec. 15, 1992 to Hoffman et al., herein incorporated by reference. Drum 108 includes surface grooves 110. Drum 108, as illustrated in FIG. 7, includes four surface grooves 110, but any number of surface grooves 110 may be included. The surface grooves 110 are spaced around the drum 108 so that each garment shell 64 eventually includes one strip 106. The web 100 travels around the drum 108 in the direction of arrow 102. The web 100 runs down into the surface grooves 110 by virtue of the fact that the drum 108 includes apertures across its surface and is under vacuum. Adhesive (shown for purposes of illustration as dots between strip 106 and the web 100 over the surface groove 110) is applied to the strip 106. Alternatively, the adhesive can be applied to the web 100 in the selected areas between leg openings 104. Suitable adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A.

The web 100 passes by the elastic application module 112 and the strip 106 of elastic is applied in a substantially unstretched condition to the web 100 over the surface groove 110. The web 100 with the strip 106 of elastic continues moving in the direction of arrow 102 out of surface groove 110 and off the drum 108. The web 100 with strip 106 of elastic passes through nip 114 to press and secure the strip 106 of elastic to the web 100. The nip 114 is defined by rolls 116 turning in the direction of arrows 118. In the alternative, any other suitable method for pressing and securing the strip 106 of elastic to the web 100 can be used. As web 100 exits the nip 114, the web 100 can be drawn at a slower rate by the downstream process than the surface speed of rolls 116, allowing the strip 106 of elastic to contract and reduce the length of web 100.

Figure 6:
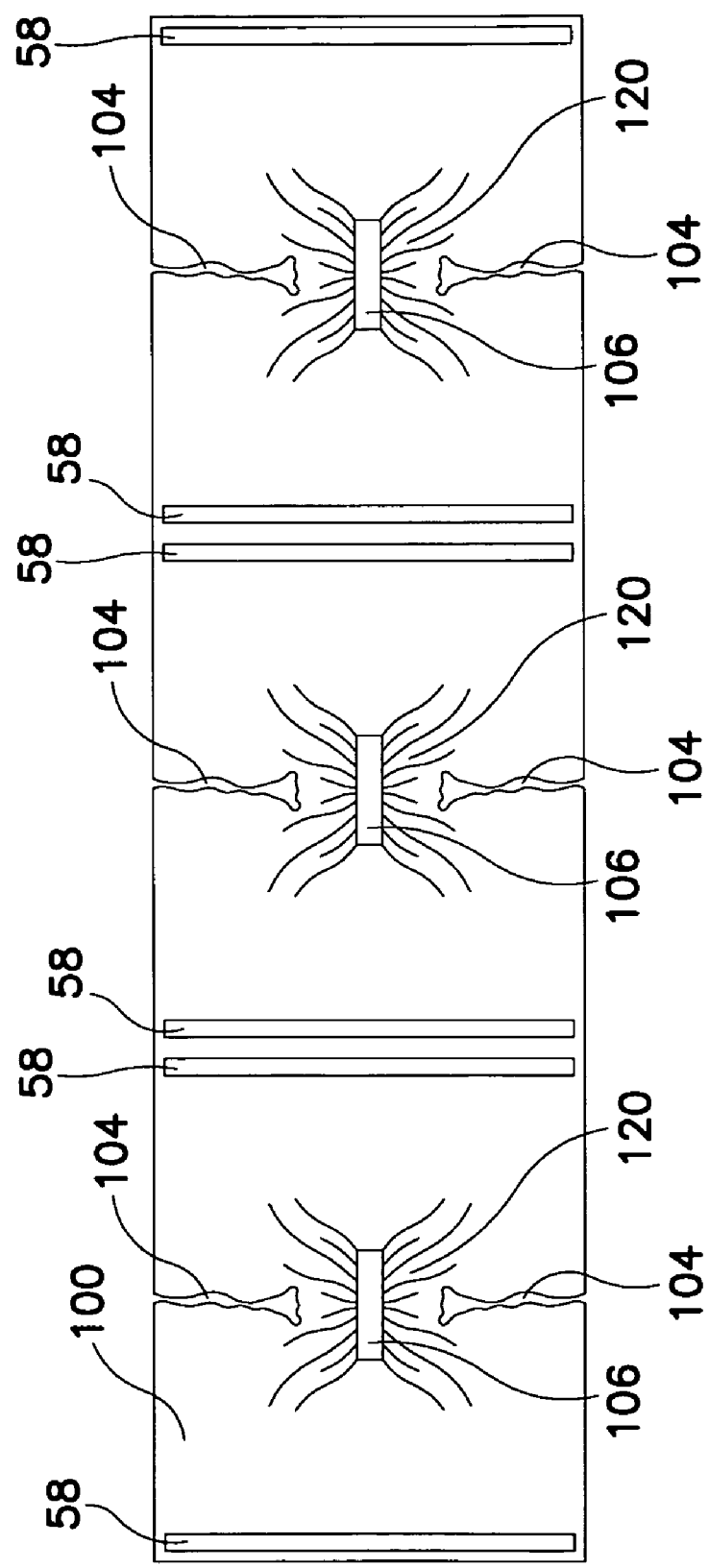
FIG. 6 is a top view of the web of FIG. 5 after contraction of the web.

FIG. 6 shows the web 100 after the contraction of the strips 106. The contraction of the web 100 defines contracted areas 120 in the selected areas between leg openings 104. The contracted area 120, as described more fully below, becomes the contracted crotch region 26 of the pant 10.

Alternatively, the strip 106 can be applied to the web 100 by any other method known in the art such as, for example, a corrugating drum such as that described in U.S. Pat. No. 4,397,704 issued 9 Aug. 1983 to Frick, or an elastic application system in which the material is gathered into folds running in the cross direction and a continuous elastic is applied in the machine direction and severed at the location of the folds in the base material such as described in U.S. Pat. No. 4,417,938 issued 29 Nov. 1983 to Sigl, or an intermittent adhesive application that allows the elastic to snap back from non-adhesive zones, a high efficiency interface roll such as that described in U.S. Pat. No. 6,022,443 issued 8 Feb. 2000 to Rajala et al., U.S. Pat. No. 5,556,504 issued 17 Sep. 1996 to Rajala et al., and U.S. Pat. No. 6,319,347 issued 20 Nov. 2001 to Rajala et al., all of which are here incorporated by reference, or by any other any means known in the art.

Figure 11:
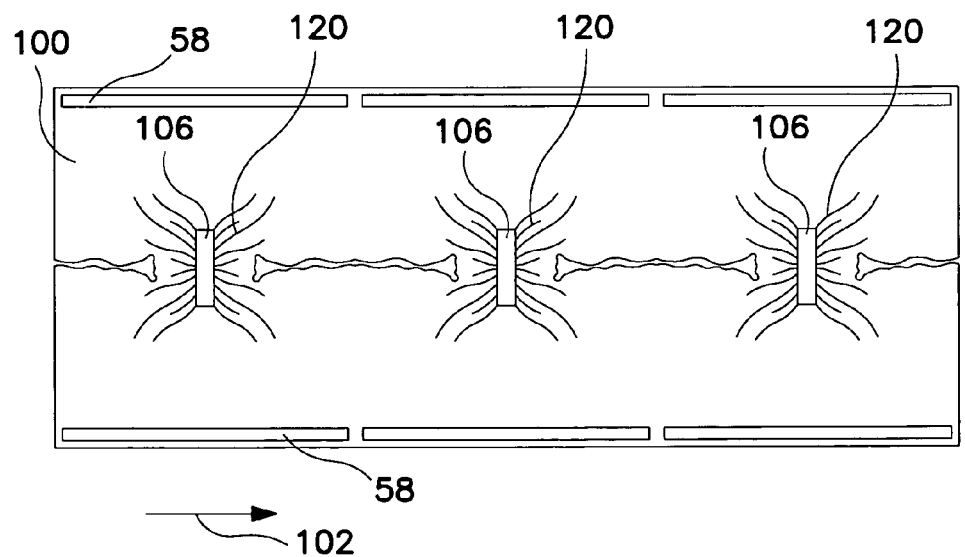
FIG. 11 is a top view of the web of FIG. 10 after contraction of the web.
Figure 12:
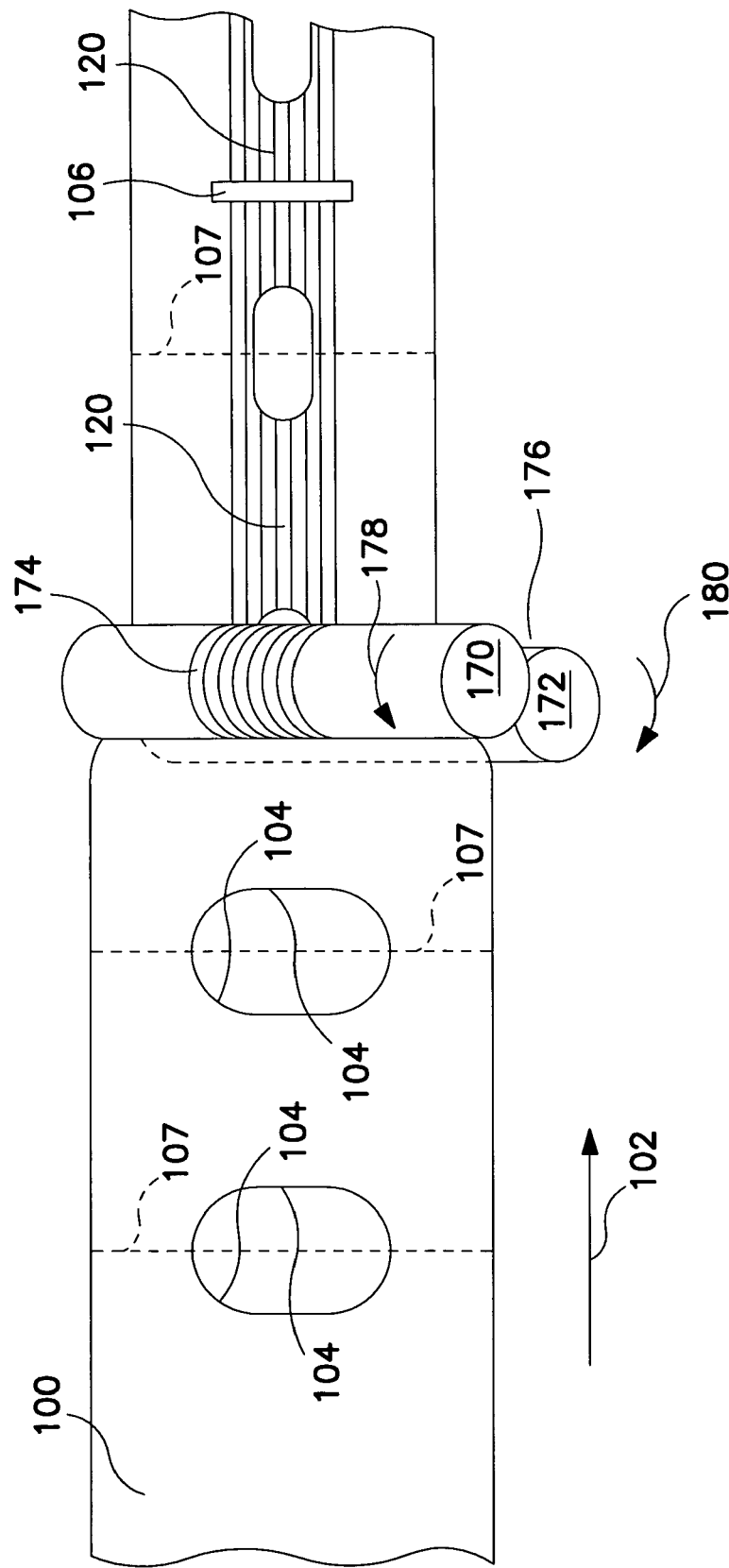
FIG. 12 is a side view of the web of FIG. 10 passing through corrugating rollers for corrugating the web of FIG. 10.

FIGS. 6 and 11 also show waist elastics 58 applied to the web 100. The waist elastics 58 can be applied by any method known in the art at any stage in the manufacturing of the pant 10.

As an alternative, the tension on the web 100 can be reduced by cutting the web 100 into separate pieces approximately midway between successive strips 106 to define a garment shell 64 (FIG. 3C). It is also contemplated, however, that the step of cutting the web 100 can be carried out after contraction of the web 100. It is further contemplated that, instead of a continuous web of multiple garment assemblies connected to one another, the web 100 may exist as a single garment assembly or garment shell 64 at the outset of the process. This option exists in both the machine direction process as well as the cross direction process.

Figure 8:
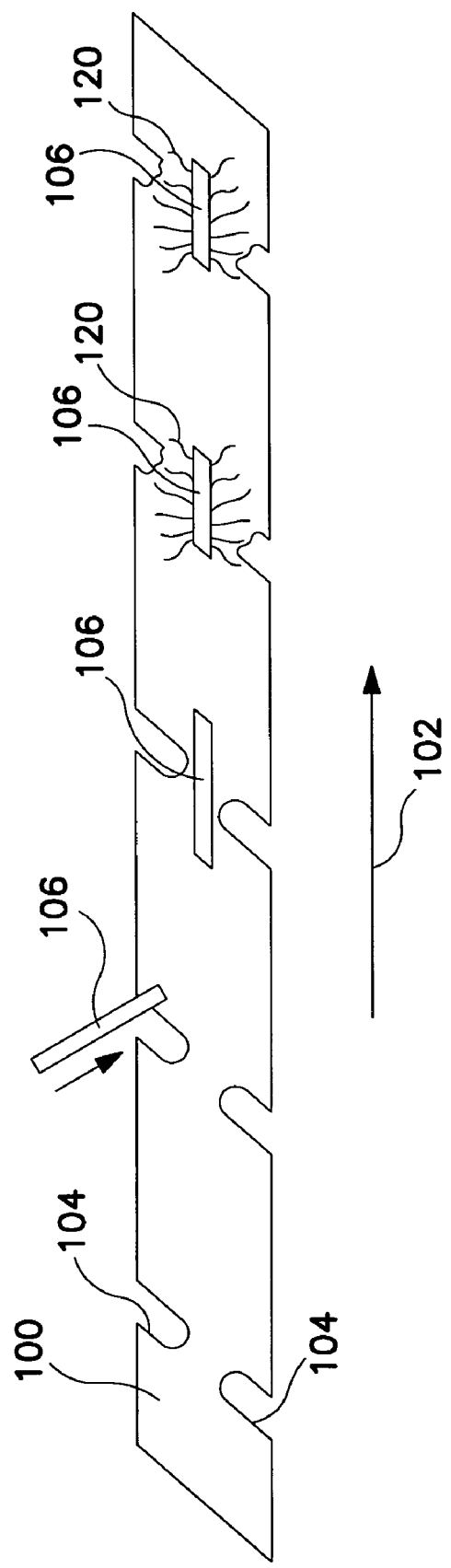
FIG. 8 is a side view of a process for applying a strip to the web.
Figure 9:
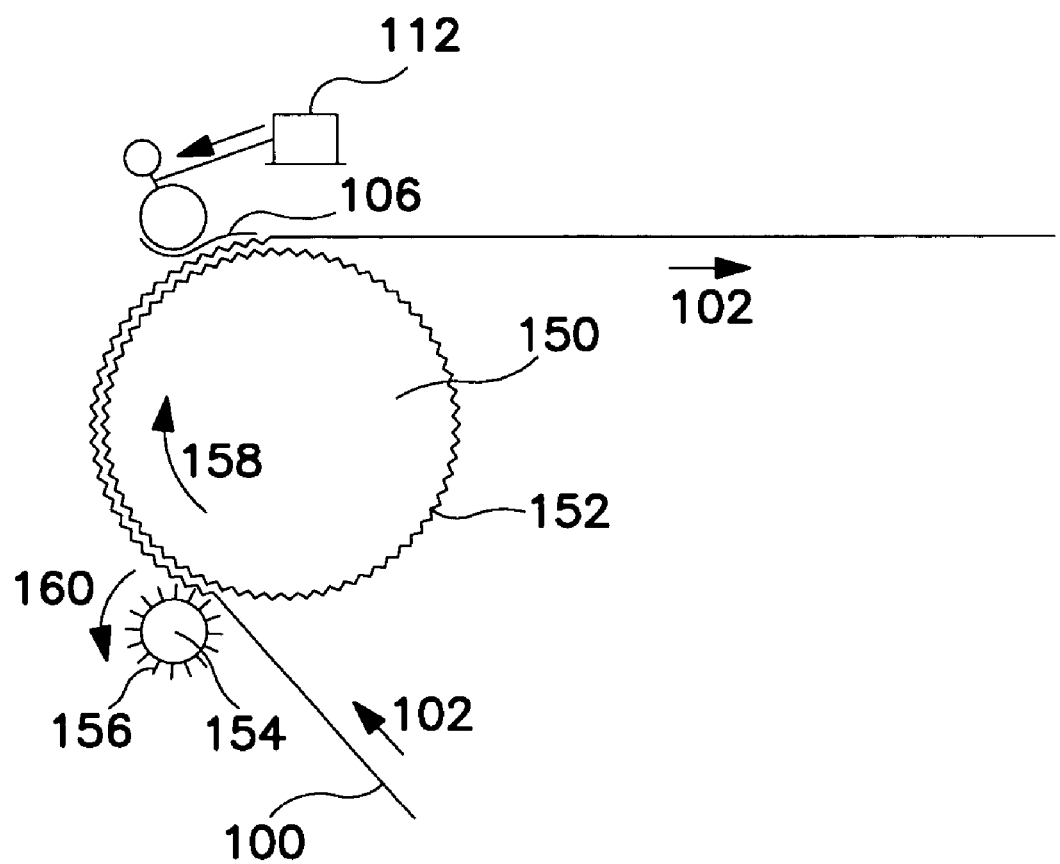
FIG. 9 is a side view of a corrugating drum for corrugating the web of FIG. 5.

Referring to FIG. 8, the strips 106, whether elastic or nonelastic, can be applied to the selected areas of the web 100 between the leg openings 104 by a cut-and-place module (not shown) as is commonly known in the art.

Next, the web 100 can be contracted elastically or inelastically by any suitable means. For example, if the strip 106 is an elastic capable of delayed retraction, the web 100 can be contracted by activating the strip 106 to restore the elasticity by time, temperature, radiation or other appropriate energy. If the strip 106 is a heat shrinkable material, the web 100 can be contracted inelastically by activating the heat shrinkable material by applying heat or other appropriate energy.

In particular embodiments, the strips 106 may be applied to the web 100 after contraction or pregathering of the web 100. In the machine direction, the web 100 can be pregathered by corrugating in the selected areas between the leg openings 104 by using a corrugating drum 150 (FIG. 9) in preparation for attachment of strip 106. Corrugating drums like corrugating drum 150 are known and are described, for example, in previously mentioned U.S. Pat. No. 4,397,704 issued 9 Aug. 1983 to Frick. Alternatively, a drum with discontinuous grooves that correlate with the location of strips 106 can be used. The web 100 travels around the drum 150 in the direction of arrow 158. Pressing roll 154 has teeth 156. The web 100 is pushed down into the grooves 152 by the teeth 156, thereby corrugating the web 100. Drum 150 and pressing roller 154 move in the direction of arrows 158 and 160, respectively.

Next, the strips 106 can be applied to the corrugated web 100 by a conventional cut-and-place applicator or other appropriate apparatus. Strips 106 can be attached to the web 100 using adhesive, thermal or ultrasonic bonding, or other means known in the art. Use of a corrugating drum or other device to pregather the web 100 permits the use of an unstretched elastic or of a non-elastic, non-retractive material such as a film or nonwoven material with properties similar to the web 100. Alternatively, the strip 106 may include any of the previously described materials. The strips 106 maintain the corrugation in the contracted area 120 (FIG. 6).

In the cross direction process (FIGS. 10-12), as in the machine direction process, strips 106 can be applied to the selected areas located between the leg openings 104. In the cross direction assembly process, strips may be applied on the web 100 in an orientation perpendicular to arrow 102, as shown in FIG. 10.

The application of strip 106 of elastic material can be accomplished by a variety of methods, such as by moving the distal edges of the web 100 closer together and allowing the center portion of the web to become looped using the same principles of the previously described looper drum, but with the strip 106 being applied in an orientation perpendicular to arrow 102, or by other methods as are known in the art. As with the previously described looper drum, the web 100 can be fully extended again after application of the strip 106 in order to fully adhere the strip 106 to the web 100. In alternative embodiments, the strips 106 can be applied to the web 100 by a process in which an elastic or inelastic piece of material is cut, rotated and placed onto the web 100, for example, as described in U.S. Pat. No. 5,716,478 issued 10 Feb. 1998 to Boothe et al., U.S. Pat. No. 5,759,340 issued 2 Jun. 1998 to Boothe et al. and U.S. Pat. No. 4,608,115 issued 26 Aug. 1986 to Schroth et al., all of which are herein incorporated by reference, or by any other means known in the art. Where the strip 106 is a heat contractible material or a material capable of delayed retraction, the strip can be applied to web 100 as the web travels in the direction of arrow 102 (FIG. 10) in a flat and unlooped state.

The web 100 can be contracted elastically or inelastically by any of the previously described methods. FIG. 11 shows the web 100 after the contraction of the strips 100. The contraction of the web 100 defines contracted area 120 in the selected areas between the leg openings 104. The contracted area 120, as described more fully below, becomes the contracted crotch region 26 of the pant 10.

In particular embodiments, the strips 106 are applied to the web 100 after contraction or pregathering of the web 100. In the cross direction, the web 100 can be pregathered by corrugating in the selected areas between the leg openings 104 by using intermeshing grooved rollers 170 and 172 (FIG. 12) in preparation for attachment of strip 106. Intermeshing grooved rollers like 170 and 172 are known in the art and are described, for example, in U.S. Pat. No. 5,755,902 issued 26 May 1998 to Reynolds, herein incorporated by reference. Roller 170 includes grooves 174 only in the middle portion of the roll to correspond to the desired location of the contracted area 120 on the web. The web 100 travels through nip 176 formed by rolls 170 and 172 in the direction of arrow 102. Roller 172 has complementary grooves (not shown) designed to intermesh with grooves 174 of roller 170. The web 100 is pushed into the grooves 174 by the complementary grooves on roll 172 to provide the corrugation in the contracted area 120. Rolls 170 and 172 move in the direction of arrows 178 and 180, respectively. The corrugations are held in place by attaching strips 106 on top of the corrugations.

The strip 106 can be applied to the corrugated web 100 by a cut-and-place module, or similar technology, as is commonly known in the art and can be attached to the web using thermal, ultrasonic or adhesive bonding, or any other means known in the art. The strip 106 may include an inextensible material such as a film or nonwoven material with properties similar to web 100, or may include any of the previously described materials.

In either the machine direction process or the cross direction process, the web 100 can now be cut into individual pieces, each of which will form a garment shell 64. The cutting can be accomplished by, for example, pinch cutting, shear cutting, or any other means known in the art. As another alternative, the web 100 can be provided as separate pre-cut pieces each of which pre-cut separate pieces will eventually become a single garment shell 64, so that this cutting step could be skipped and the process could start with a pre-cut piece as the web 100. FIG. 3C shows the garment shell 64 prior to folding and formation of the side seams 54. As shown and as previously mentioned with respect to FIGS. 1, 2A, and 2B the garment shell 64 can include a front region 22, a back region 24, a crotch region 26, an inner surface 28, and an outer surface 30 (not shown), front waist edge 38, back waist edge 39, and waist elastic member 58. The garment shell 64 can also include strip 106. It is also contemplated that the garment shell 64 can be made upside-down, i.e., with the inner surface 28 facing downwardly (not shown). The garment shell 64 can then be folded and the side seams 54 formed by any conventional method known in the art to form the pant 10 (without an absorbent structure). It is contemplated that the step of contracting the web 100 can occur either before or after the step of cutting into individual garment shells 64, and also before or after the formation of the side seams 54.

In either the machine direction process or the cross direction process, in alternative embodiments, the strip 106 need not be a single strip of material. In particular embodiments, elastic strands or ribbons as are known in the art can be used instead of a single strip of material for strip 106. The elastic strands or ribbons can be straight or curved. Alternatively, the crotch region 26 may include one or more strips 106 longitudinally offset, or multiple strips 106 arranged in a segmented manner, either spaced apart longitudinally or spaced apart transversely. In certain embodiments, the strip may be, at most, one-third the length of the garment shell when the garment shell is in a laid-flat, fully extended, namely uncontracted, condition. In addition, in the embodiments in which the web is corrugated or otherwise gathered, it is contemplated that instead of attaching a strip 106, the corrugation or gathers in the contracted area 120 can be maintained by fusing or bonding the corrugations together in the selected areas between the leg openings 104. The corrugations can be bonded to themselves to hold them in place by adhesive, thermal, or pressure bonding, or by any other means known in the art.

In the machine direction process, the strip 106 need not be a separate piece of material applied to the web 100. Instead, the web 100 may include an integral elastic zone aligned along the machine direction center line, instead of strip 106, with the elastic zone active in only the crotch region. Elasticization of only the crotch region of the pant may be achieved by, for example, an elastic laminate structure in which the elastic is attached to the laminate using an intermittent adhesive. Intermittent adhesive application would allow the elastic to snap back from non-adhesive zones, which would be uncontracted as a result; contracted, adhesive-bearing zones can be located only in the crotch region of the garment. As an alternative, the elastic nature of certain regions may be inactivated by chopping or overbonding the elastic or other methods known in the art, for example, as described in U.S. Pat. No. 6,248,097 issued 19 Jun. 2001 to Beitz, herein incorporated by reference.

Referring to FIGS. 2A, 2B, 3A, and 3B in particular embodiments, an absorbent structure 60 is included in the pant 10. The absorbent structure 60 can be introduced into the pant 10 in any suitable manner known in the art. In particular embodiments, the absorbent structure 60 can be placed on top of the crotch region 26 on the inner surface 28 of the garment shell 64, either prior to formation of side seams 54 or after side seams 54 are made. It is also contemplated, however, that the absorbent structure 60 can be attached prior to contracting and/or cutting the web 100. Where the absorbent structure 60 is added to the pant 10 prior to formation of side seams 54, cut-and-place methods such as are known in the art may be used. Alternatively, for a closed pant (i.e., side seams already formed), the absorbent structure 60 may be inserted into the pant such as by the method described in the PCT Publication WO 02/52967 by Rabe, et al., or by other means as may be known in the art. The absorbent structure 60 can be attached to the garment shell 64 at the front waist edge 38 and back waist edge 39, or at some point below the front waist edge 38 and back waist edge 39 on the front region 22 and back region 24. Additionally or alternatively, the absorbent structure 60 can be attached in the crotch region 26. The attachment can be accomplished by ultrasonic or adhesive bonding, or any other suitable method known in the art. As shown in FIGS. 2A and 2B, attachment to the front and back regions 22 and 24 provides for a loose fit of shell 64 in the crotch region 26, while the absorbent structure 60 is still held close to the body.

In particular embodiments, the absorbent structure 60 is stretchable or elasticizable in order to provide the desired close to the body fit for the absorbent structure 60 while the garment shell 64 hangs loosely. Alternatively, a suspension system for the absorbent structure may be required to provide a loose fit for the garment shell 64, such as described in U.S. Pat. No. 6,168,585 issued 2 Jan. 2001 to Cesco-Cancian, herein incorporated by reference.

The garment shell 64 with the absorbent structure 60 can then be folded and the side seams 54 formed by any conventional method known in the art to form the pant 10, as shown in FIGS. 2A and 2B. After folding the garment shell 64 and forming the side seams 54 (with or without an absorbent structure 60), if a temporarily inhibited elastic or latent elastic is used as the waist elastic 58, it may need to be activated to restore the elasticity. Alternatively, the elastics may be activated prior to seaming.

Figure 14A:
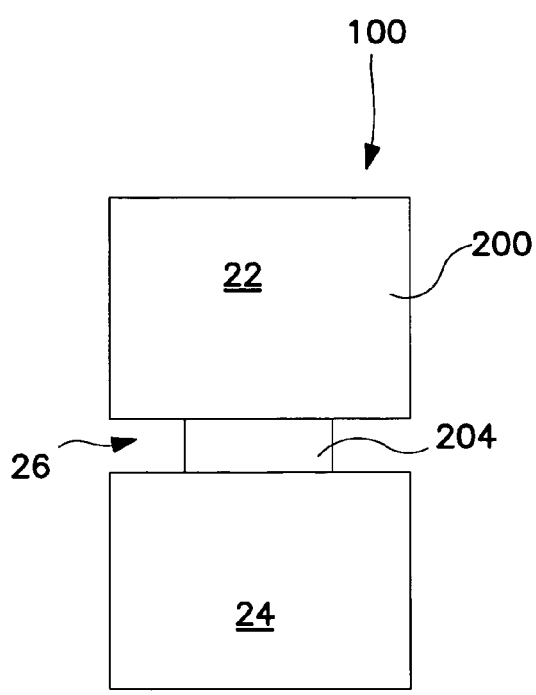
FIGS. 14A-14D are top views of multi-piece webs.
Figure 14B:
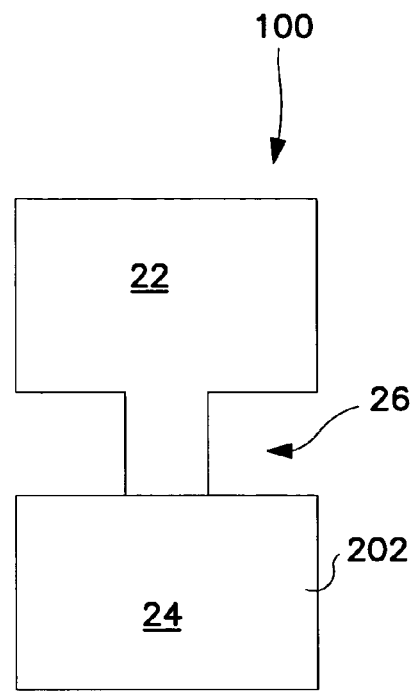
Figure 14C:
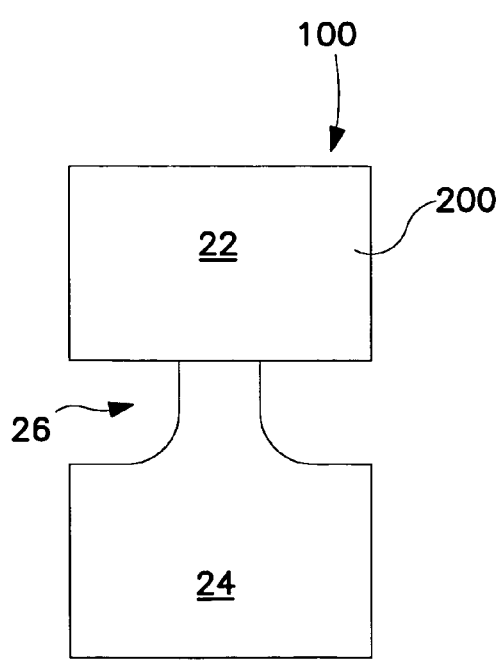
Figure 14D:
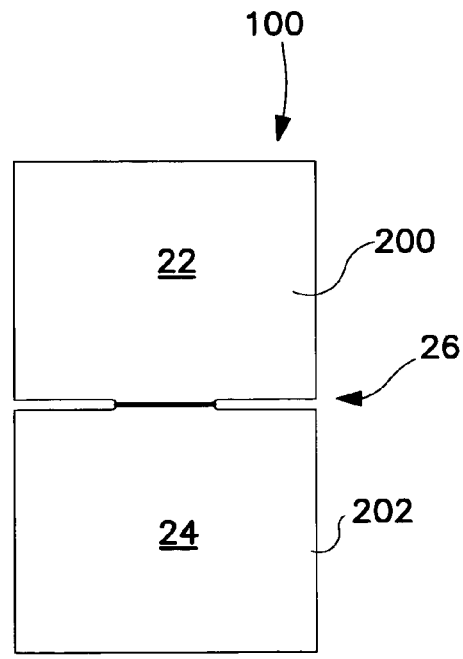

In certain embodiments, the web 100 may be a multi-piece web. More particularly, the front region 22, the back region 24, and/or the crotch region 26 may include separate panels of material, namely a front panel 200, a back panel 202, and/or a crotch panel 204, as illustrated in FIGS. 14A, 14B, 14C, and 14D. The multi-piece web 100 may be formed using either cross direction assembly, in which live elastics may be used to create a functional waistband, or using machine direction assembly, in which cut-and-place technology may be used with a latent waistband material. Alternatively, the multi-piece web 100 may be formed by conveying the crotch panel 204 and the absorbent structure 60 (if present), and any associated gasketing devices, such as leg elastics and/or containment flaps 62 with elastics, with longitudinal axis 48 oriented in the machine direction. This sub-assembly could then be turned 90 degrees and attached to the front and back panels 200, 202, which are both being run with their longitudinal axes parallel to the cross direction. Alternatively, the web 100 may include separate front and back panels 200, 202 connected to one another in the crotch region 26, as illustrated in FIG. 14D.

The hanging legs may be enhanced by any of a variety of leg extensions. Suitably, at least a portion of the hanging legs is non-planar when the garment is in a laid flat configuration prior to formation of the side seams. More particularly, material segments may be applied to the web 100 to deliver inner-leg fit and crotch depth in relatively process-friendly ways. The material segments are designed to be able to expand in areas where a single web may be unable to provide a satisfactory three-dimensional fit to the contours of the wearer's body.

One example of a leg extension is illustrated in FIGS. 15A, 15B, and 15C. This type of leg extension includes a shaped crotch panel 204 attached to the front region 22, the back region 24, and/or the crotch region 26 over a transverse axis of the web 100. The web 100 may be partially or completely slit along the transverse axis beneath the shaped crotch panel 204. Alternatively, the web 100 may include separate front and back panels 200, 202, either maintained separately, as shown in FIG. 15C, or partially joined to one another along the transverse axis of the web 100 beneath the shaped crotch panel 204, as shown in FIG. 15B. The leg openings 104 are at least partially defined between the front and back regions 22, 24 when the garment is in a laid-flat configuration. The leg openings 104 may be formed by simple slits and/or by cut-outs.

The shaped crotch panel 204, if provided as a single piece, may be in the shape of a bowtie, essentially two triangles joined together at one point of each triangle. More particularly, the shaped crotch panel 204 may have a narrower longitudinal length in the central region 206 than in the distal regions 208 of the crotch panel 204 when laid flat. The shaped crotch panel 204 may be pre-contoured in the bowtie shape with upper and lower edges 210, 212 of the bowtie brought together along the distal regions 208 such that the upper and lower edges 210, 212 are generally parallel to one another, and then bonded to the web 100 in this position, as illustrated in FIG. 15A. Alternatively, the shaped crotch panel 204 need not have the shape of a bowtie to begin with, but instead may be folded in the same manner as described, with the upper and lower edges 210, 212 brought toward one another along distal regions 208, but with the central zone of the crotch panel 204 remaining essentially flat along a longitudinal centerline of the crotch panel, and then bonded in this position. Excess material above and below the bonds may then be trimmed and discarded. Regardless of the original shape of the crotch panel 204 in these embodiments, whether a bowtie or rectangular, the resulting bonds that attach the crotch panel 204 to the web 100 essentially form the bowtie shape along the crotch panel 204, which may be seen if the crotch panel 204 were spread flat after bonding. More particularly, when the crotch panel 204 is spread flat, the distance between bonded regions of upper and lower edges 210, 212, measured parallel to longitudinal axis 48, is shorter along the central region 206 of the crotch panel 204 and longer in the distal regions 208 of the crotch panel 204, thus forming the bowtie shape. The shaped crotch panel 204 provides a greater amount or length of material, measured parallel to longitudinal axis 48, at the lower leg edge than along the longitudinal centerline of the garment in the crotch region 26. As in the embodiments described above, the web 100 may also be contracted along at least a portion of the longitudinal centerline of the web 100.

Figure 16A:
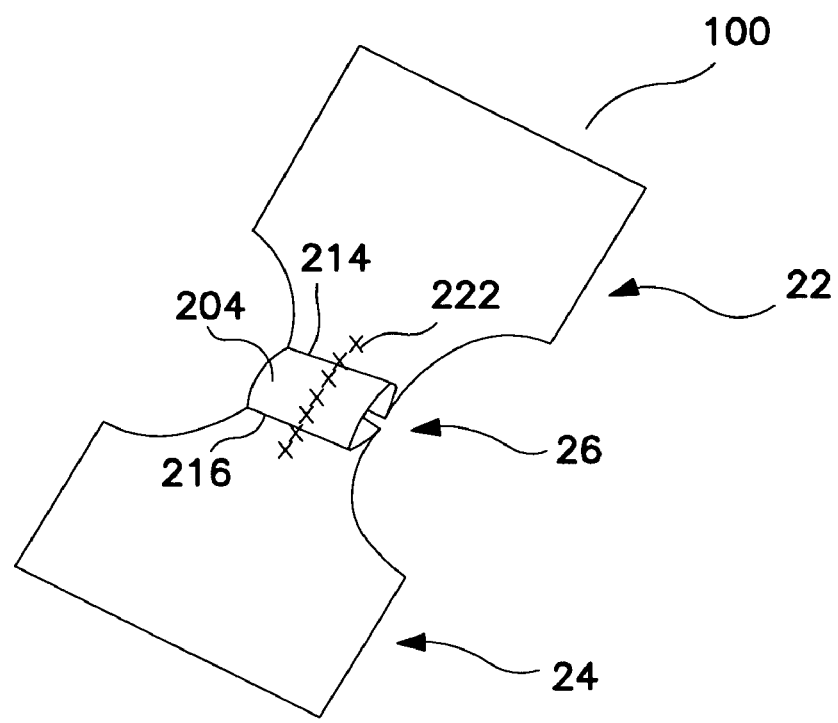
FIG. 16A is a perspective view of a garment having a folded crotch panel.
Figure 16B:
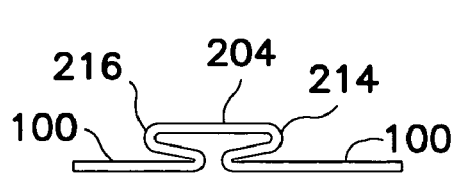
FIGS. 16B and 16C are side views of garments having folded crotch panels.
Figure 16C:
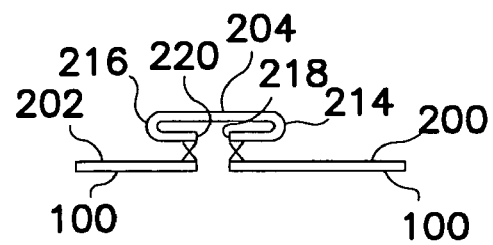

Similar examples of leg extensions are illustrated in FIGS. 16A, 16B, and 16C. As shown, in these embodiments the crotch panel 204 has a uniform width in the longitudinal direction and is folded rather than pre-contoured. More particularly, the crotch panel 204 is separated from the underlying web 100 by folds 214, 216. For example, the web 100 and the crotch panel 204 may be a single web of material separated by folds 214 and 216 (as well as any underlying folds), which are parallel to the transverse axis 49 of the garment, as shown in FIGS. 16A and 16B. Alternatively, the crotch panel 204 may include a piece of material separate from the web 100, in which case the crotch panel 204 is folded, such as in a C-fold configuration shown in FIG. 16C, with longitudinally opposed edges of the crotch panel 218, 220 attached to the underlying web 100. The underlying web 100 may be a single piece of material slit along transverse edges of the web, either partially or across a full transverse width of the web 100. In any case, the leg openings are formed between the front and back regions of the web 100. Alternatively, the underlying web 100 may include separate front and back panels 200, 202, either maintained separately from one another or at least partially joined to one another in the crotch region 26.

The folded crotch panel 204 may be stabilized along a longitudinal centerline of the web 222, such as by bonding the crotch panel 206 to the underlying web 100 along the longitudinal centerline of the web, as shown in FIG. 16A, and/or by applying an overlying material strip (not shown) along the longitudinal centerline of the web, or any other suitable attachment methods. Any of the above-described leg opening shapes as well as longitudinal contracting may be applied to the folded crotch panel embodiments. The folded crotch panel embodiments may be quite amenable to simplified processing, such as in a continuous fashion, at least when the longitudinal axis of the garment is oriented perpendicular to the machine direction.

Figure 17A:
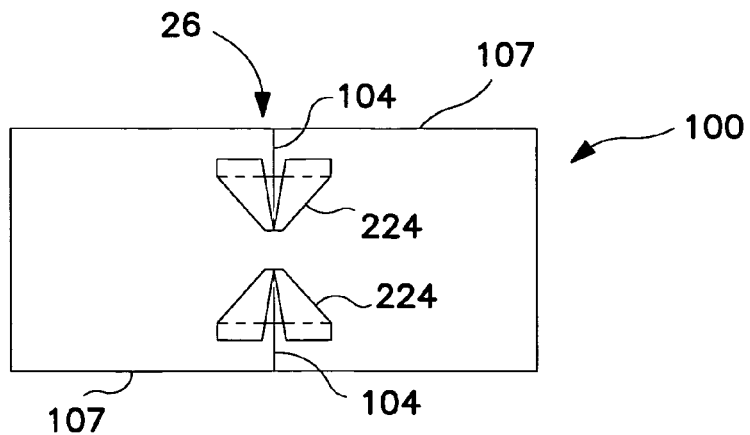
FIGS. 17A and 17E are top views of garments having leg extension strips.
Figure 17B:
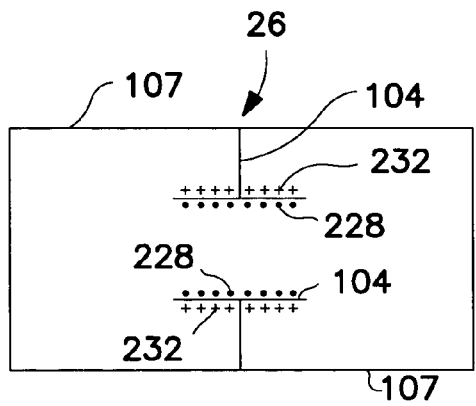
FIGS. 17B-17D are top views of pieces of the garment in FIG. 17A prior to completing assembly of the garment.
Figure 17C:
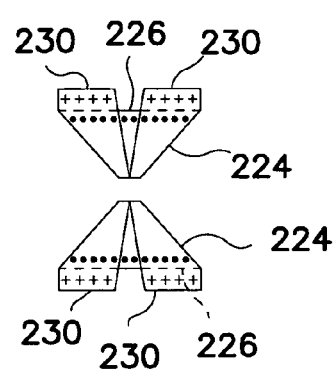
Figure 17D:
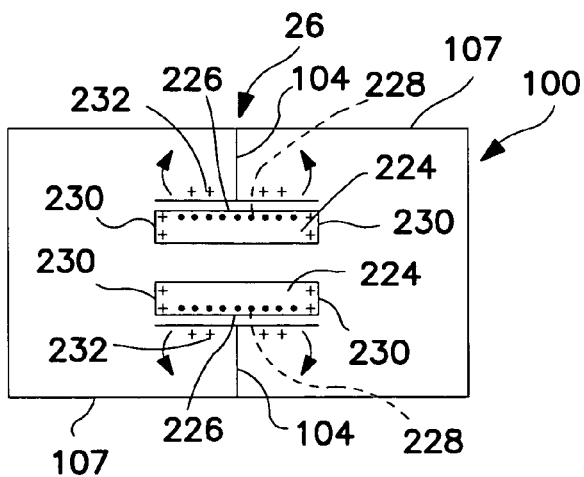
Figure 17E:
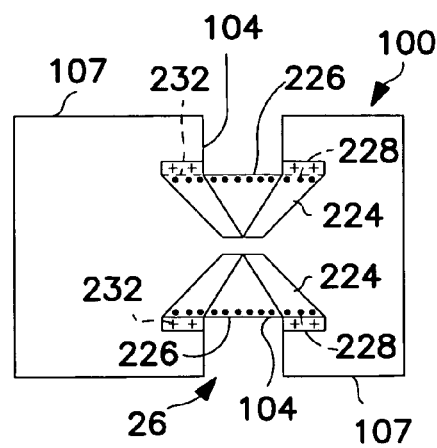

Other examples of leg extensions are illustrated in FIGS. 17A-17E. In these embodiments, the web 100, either a single web or a multi-piece web, includes a T-shaped cut along each of the transversely opposed edges 107 of the web defining the leg openings 104. The T-shape may be a simple slit, as shown in FIGS. 17A, 17B, and 17D, or a portion of the web 100 may be removed along the distal portions of the "T" shape along the transversely opposed edges, as shown in FIG. 17E. Two separate strips 224 of material, as illustrated in FIGS. 17C-E, are each attached to the web 100 in the crotch region 26 with a portion of a longitudinal edge 226 of the strip 224 attached along an interior longitudinal edge 228 of one of the T-shaped cuts to form hanging inner thighs on the garment. Dots indicate this set of bonds. This step of the process is illustrated in particular in FIG. 17D. The strips 224 are folded (in the direction of the arrows in FIG. 17D) such that each of two transverse edges 230 of each strip 224 are then bonded along a distal longitudinal edge 232 of each T-shaped cut, such that this set of bonds is parallel to the bonds along the longitudinal edge 226 of the strip 224, with this set of bonds indicated by plus marks in FIGS. 17B and 17C. The strips 224 are shown in their folded position in FIG. 17C, but the strips 224 may or may not be pre-folded in this manner prior to bonding. Bonding along the longitudinal and transverse edges 226, 230 of the strips 224 may be carried out sequentially or simultaneously, with the choice of sequence possibly influencing whether adhesive or other bonding types would be suitable. The resulting garment provides a square profile as viewed through the crotch region 26, since the web 100 suitably has some width between the applied strips 224. This width may be of use for supporting and concealing an absorbent structure 60.

Figure 18A:
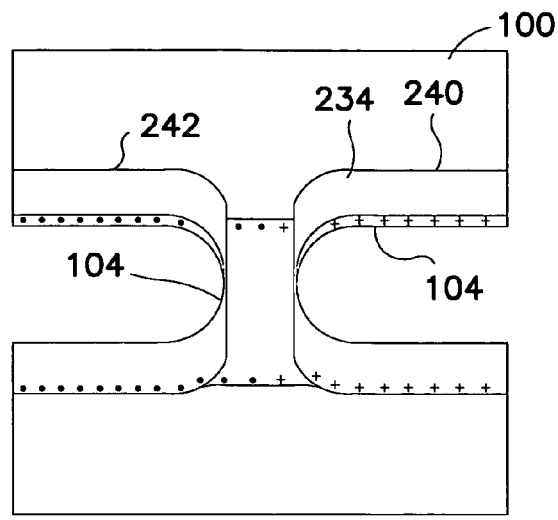
FIG. 18A is a top view of a garment having a leg extension strip.
Figure 18B:
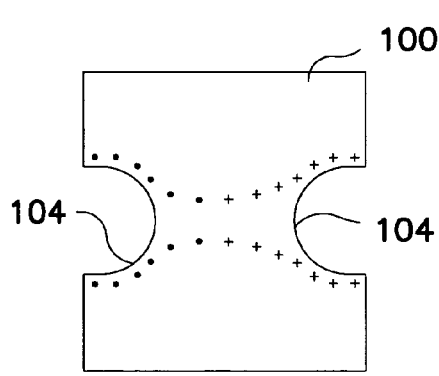
FIGS. 18B-18F are top views of pieces that may be used to form a garment similar to the garment in FIG. 18A.
Figure 18C:
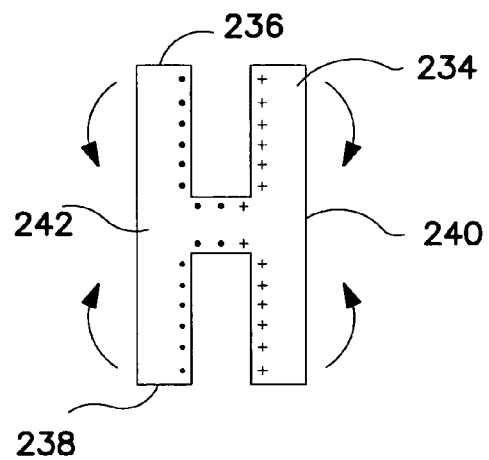
Figure 18D:
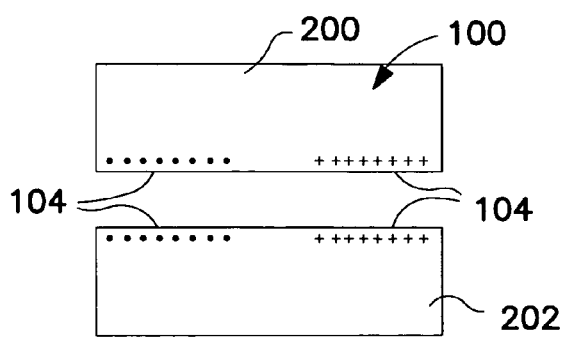
Figure 18E:
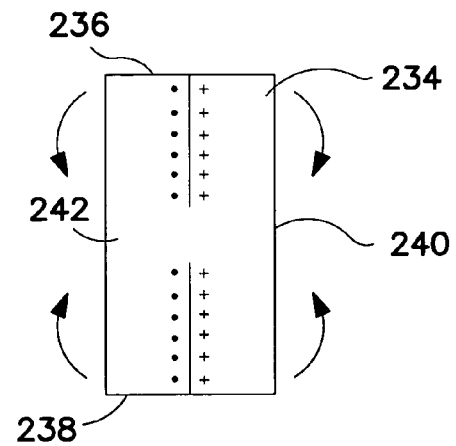
Figure 18F:
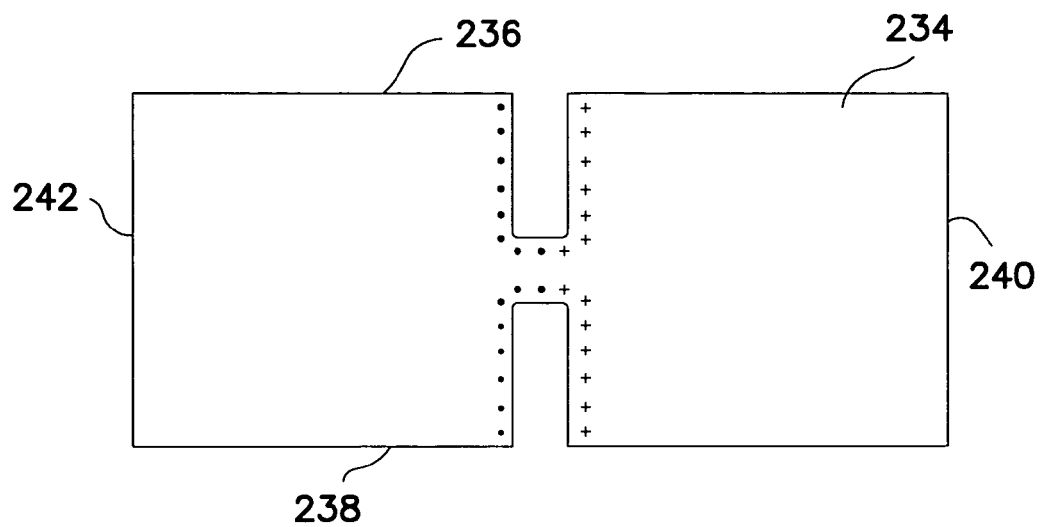

Additional examples of leg extensions are illustrated in FIGS. 18A-18H. In the embodiments in FIGS. 18A-18F, a single strip 234 of material can be cut along each of two longitudinally opposed edges 236, 238 of the strip 234. Examples of suitable strips 234 are shown in FIGS. 18C, 18E, and 18F. This concept can provide leg lengths of any selected amount, including full-length pants. For example, the strips 234 in FIGS. 18C and 18E would result in shorter pant legs, whereas the strip 234 in FIG. 18F could be used to make full-length pant legs. The edges of each cut portion of the strip 234 are attached to opposite leg openings 104 on the web 100, as shown in FIGS. 18A-18F, with corresponding sets of bond points between the strip 234 and the web 100 indicated as plus signs and dots, such that the plus signs on the strip 234 match up with the plus signs on the web 100 and the dots on the strip 234 match up with the dots on the web 100. At least a portion of each of the longitudinally opposed edges 236, 238 of the strip 234 ends up being laterally oriented in the resulting pant. The resulting pant includes the transversely opposed edges 240, 242 of the strip 234 extending from the web 100 in a three-dimensional manner.

As shown in FIGS. 18A, 18B, and 18C, the leg openings 104 may include cut-outs, which can provide a square-profile crotch as described above. In embodiments having a web 100 as shown in FIG. 18B, the resulting crotch region 26 includes a layer of the web as well as a layer of the strip 234. Alternatively, as shown in FIGS. 18D and 18E, the web 100 may include separate front and back panels 200, 202, which results in a crotch region 26 formed of the strip 234.

Figures 18G, 18H:
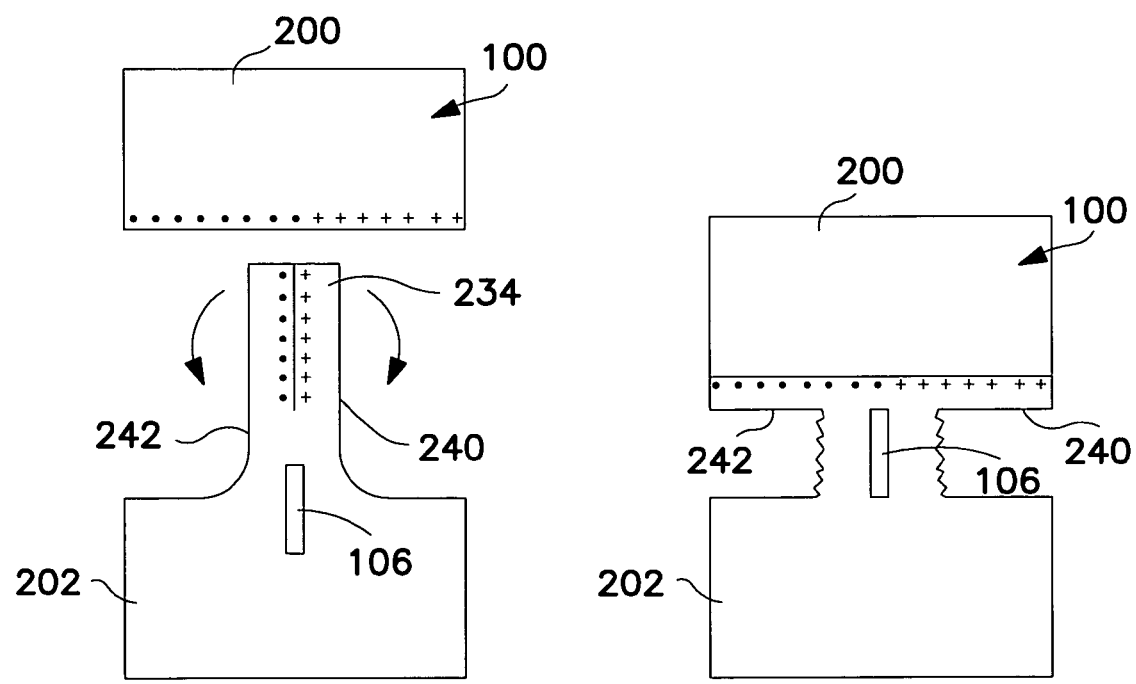
FIG. 18G is a top view of pieces that may be used to form a garment.
FIG. 18H is a top view of a garment that may be formed from the pieces in FIG. 18G.

In the embodiments in FIGS. 18G and 18H, the strip 234 may be integral with the front panel 200 or the back panel 202. The strip 234 can be cut along a longitudinal centerline of the pant assembly. The edges of each cut portion of the strip 234 are folded apart from one another in the direction of the arrows shown in FIG. 18G and are attached to a leg opening 104 edge on the web 100, with corresponding sets of bond points between the strip 234 and the web 100 indicated as plus signs and dots. The resulting pant, illustrated in FIG. 18H, includes the transversely opposed edges 240, 242 of the strip 234 extending from the web 100 in a three-dimensional manner. The crotch region 26 may be contracted such as with a strip 106, as described in detail above.

Figure 19A:
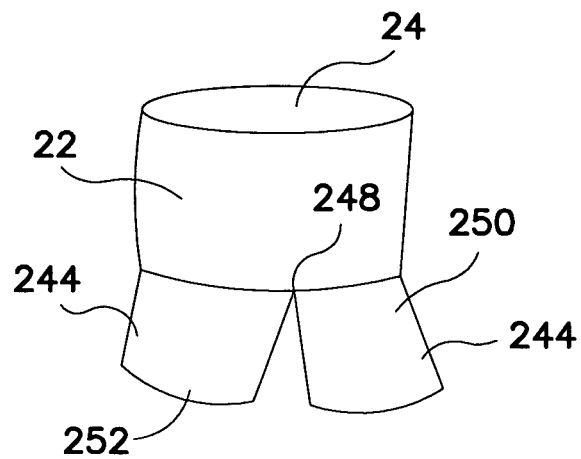
FIGS. 19A-19C are perspective views of a garment, and portions of a garment, having leg extensions.
Figure 19B:
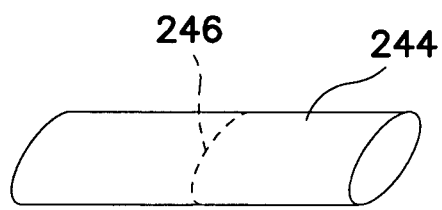
Figure 19C:
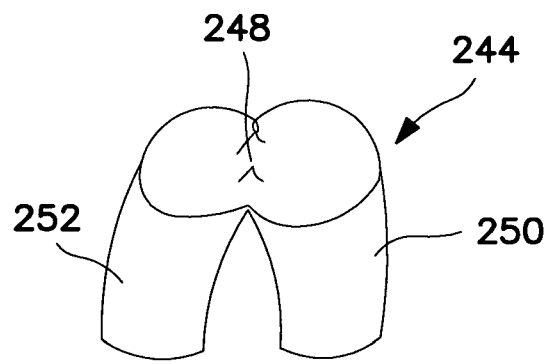

Yet another example of leg extensions is illustrated in FIGS. 19A, 19B, and 19C. In these embodiments, a tube 244 of material, as shown in FIG. 19B can be used to provide pant legs of any desired length. The tube 244 is partially cut along a circumference 246 of the tube 244 and folded open, thereby exposing an uncut crotch portion 248 that connects the two resulting pant legs 250, 252, as shown in FIG. 19C. The open ends of the tubes 244 at the cut ends are the tops of the leg openings 52. Front and back regions 22, 24 of a web 100 can then be attached to the two pant legs 250, 252, as shown in FIG. 19A.

For any of the leg extension concepts described, the web 100 may be either a single web or a multi-piece web, if consistent with the respective concept. Additionally, the web 100 may be contracted along at least a portion of the longitudinal centerline of the web 100, if consistent with the respective concept.

For any of the boxer garment concepts described, the separate pieces of material may have differing properties from one another. For example, a crotch panel may be elastomeric or extensible while the remaining web materials may be inextensible or inelastic. As another example, leg extension materials may be made of an inelastic or inextensible material while the torso section of the garment may be elastomeric or extensible.

The various components of the pant can be connected together by any means known to those skilled in the art such as, for example, adhesive, thermal and/or ultrasonic bonds, pressure bonds and also sewing and other methods used in durable garment manufacturing. Most of the components may be connected using ultrasonic bonding for improved manufacturing efficiency and reduced raw material costs. For example, in particular embodiments, the side seams 54 are made using ultrasonic bonding. Certain garment manufacturing equipment which is readily known and understood in the art, including frames and mounting structures, ultrasonic and adhesive bonding devices, transport conveyors, transfer rolls, guide rolls, tension rolls, and the like, have not been shown in the Figures.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A pant made from a web, the pant comprising:
   a boxer shorts garment shell, the garment shell including a front region, a back region, a crotch region between the front region and the back region, a front waist edge, a back waist edge, side seams connecting the front region to the back region, two leg openings and hanging legs, a crotch panel attached to at least one of the front region, the back region, and the crotch region, wherein a distance between bonded regions of upper and lower edges of the crotch panel, measured parallel to a longitudinal axis of the pant, is shorter along a central region of the crotch panel and longer in distal regions of the crotch panel;
   wherein the hanging legs include no elasticization and no gathering around a full periphery of the leg openings, and at least a portion of each of the hanging legs is non-planar when the pant is in a laid flat configuration prior to formation of the side seams.

2. The pant of claim 1, wherein the front region and the back region comprise a single web, and the crotch region is separated from the front and back regions by folds.

3. The pant of claim 2, wherein the crotch region comprises a crotch panel stabilized along a longitudinal centerline of the web by a bond to the web along the longitudinal centerline.

4. The pant of claim 1, further comprising a separate crotch panel attached to the front region and the back region, wherein the crotch panel is stabilized along a longitudinal centerline of the web.

5. The pant of claim 1, wherein the hanging legs comprise leg extensions attached to the front region and the back region.

6. The pant of claim 5, wherein the leg extensions comprise an inelastic material, and the front and back regions comprise an extensible material.

7. The pant of claim 5, wherein each of the leg extensions comprises a strip attached to the crotch region of the garment shell along a longitudinal edge of the strip, and folded with each of two transverse edges of the strip bonded parallel to the longitudinal edge of the strip.

8. The pant of claim 5, wherein the leg extensions comprise a single leg-extension web that is cut along each of two longitudinally opposed edges of the leg-extension web, with a first edge of each cut portion of the leg-extension web attached along a first leg opening of the garment shell and a second edge of each cut portion of the leg-extension web attached along a second leg opening of the garment shell.

9. The pant of claim 5, wherein the leg extensions comprise two tubes connected to one another in the crotch region, and each tube is connected to both the front region and the back region.

10. The pant of claim 8, wherein the garment shell comprises separate front and back regions each defining a portion of the first and second leg openings.

11. The pant of claim 1, wherein the hanging legs comprise a leg-extension web integral with one of the front and back regions, and the leg-extension web is cut longitudinally, with first and second edges along the cut portion of the leg-extension web attached along an edge of the other of the front and back regions.

12. The pant of claim 1, wherein the crotch region is contracted.

13. The pant of claim 1, wherein the front region comprises a first web and the back region comprises a second web.

14. The pant of claim 13, wherein the first and second webs are at least partially attached directly to one another in the crotch region.

15. The pant of claim 1, wherein the leg openings are formed from cuts along two transversely opposed edges of the web.

16. The pant of claim 1, further comprising an absorbent structure attached to the garment shell on at least one of the front region, the back region, and the crotch region.

17. The pant of claim 16, wherein the absorbent structure comprises a web of cellulosic fibers mixed with particles of a superabsorbent hydrogel-forming material.

18. The pant of claim 1, wherein the crotch panel comprises a web of a same material as the web of the front region and the back region.

19. The pant of claim 1, wherein the crotch region is contracted by a strip.

20. The pant of claim 19, wherein the strip includes heat contractible materials or delayed retraction materials.

* * * * *